United States Patent
Yu et al.

(10) Patent No.: US 10,875,822 B2
(45) Date of Patent: Dec. 29, 2020

(54) DIRECTED β-C(SP³)#H IODINATION AND ARYLATION OF KETONES

(71) Applicant: The Scripps Research Institute, La Jolla, CA (US)

(72) Inventors: Jin-quan Yu, San Diego, CA (US); Ru-yi Zhu, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/639,401

(22) PCT Filed: Aug. 13, 2018

(86) PCT No.: PCT/US2018/046465
§ 371 (c)(1),
(2) Date: Feb. 14, 2020

(87) PCT Pub. No.: WO2019/036349
PCT Pub. Date: Feb. 21, 2019

(65) Prior Publication Data
US 2020/0255363 A1 Aug. 13, 2020

Related U.S. Application Data

(60) Provisional application No. 62/546,166, filed on Aug. 16, 2017.

(51) Int. Cl.
C07C 45/42 (2006.01)
C07C 249/12 (2006.01)
B01J 31/22 (2006.01)
C07C 49/233 (2006.01)

(52) U.S. Cl.
CPC .......... *C07C 45/42* (2013.01); *B01J 31/2226* (2013.01); *C07C 249/12* (2013.01); *B01J 2531/0219* (2013.01); *B01J 2531/824* (2013.01); *C07C 49/233* (2013.01)

(58) Field of Classification Search
CPC ..... C07C 45/42; C07C 249/12; C07C 49/233; B01J 31/2226; B01J 2531/824; B01J 2531/0219
See application file for complete search history.

(56) References Cited

U.S. PATENT DOCUMENTS

| | | |
|---|---|---|
| 4,305,923 A | 12/1981 | Weiler et al. |
| 7,057,067 B2 | 6/2006 | Kodama et al. |

FOREIGN PATENT DOCUMENTS

| | | |
|---|---|---|
| CN | 111212824 | 5/2020 |
| WO | WO-2019036349 A1 | 2/2019 |
| WO | WO-2019036349 A8 | 5/2019 |

OTHER PUBLICATIONS

"International Application Serial No. PCT/US2018/046465, International Search Report dated May 24, 2018", 2 pgs.
"International Application Serial No. PCT/US2018/046465, Written Opinion dated May 24, 2018", 4 pgs.
Carr, Kathryn, et al., "Substitution at the 4-Methyl of Lanost-8-en-3-one", Journal of the Chemical Society, Chemical Communications, Issue 18, (1984), 1227-1228.
Gulia, Nurbey, et al., "Palladium-Catalyzed Pyrazole-Directed sp3 C—H Bond Arylation for the Synthesis of B-Phenethylamines", Angewandte Chemie International Edition, 56 (13), (2017), 3630-3634.
Yang, KE, et al., "Catalytic C—H Arylation of Aliphatic Aldehydes Enabled by a Transient Ligand", Journal of the American Chemical Society, 138 (39), (Sep. 21, 2016).
Zhang, Fang-Lin, et al., "Functionalization of C(sp3)-H bonds using a transient directing group", Science, 351 (6270), (Jan. 15, 2016), 252-256.
Zhu, Ru-Yi, et al., "Ligand-Enabled Pd(II)-Catalyzed Bromination and Iodination of C(sp3)-H Bonds", Journal of the American Chemical Society, 139 (16), (Apr. 10, 2017), 5724-5727.

*Primary Examiner* — Jafar F Parsa
(74) *Attorney, Agent, or Firm* — Schwegman Lundberg & Woessner, P.A.

(57) ABSTRACT

This invention discloses the first example of palladium(II)-catalyzed β-C(sp³)-H iodination or arylation of a wide range of ketones by using a commercially available aminooxy-acetic acid auxiliary. This L, X-type directing group overcomes the limitation of the transient directing group approach for -βC(sp³)-H functionalization of ketones. Practical advantages of this method include simple installation of the auxiliary without chromatography, exceptional tolerance of a-functional groups, double bonds and triple bonds and rapid access to diverse sterically hindered quaternary centers.

10 Claims, 3 Drawing Sheets

Transient DG: Limited to arylation

Covalent DG: New transformation with superior scope

[a] Conditions: Substrate (0.1 mmol, 1.0 equiv), Pd(TFA)$_2$ (10 mol%), I$_2$ (1.0 equiv), PhI(OAc)$_2$ (1.0 equiv), 1,4-dioxane (1.25 mL), 40 °C, under air, 20 h. Ar$^1$ = 4-CF$_3$(C$_6$F$_4$), Ar$^1$ = 3,5-CH$_3$(C$_6$H$_3$). [b] The yield was determined by $^1$H NMR analysis of the crude product using CH$_2$Br$_2$ as the internal standard. [c] The numbers in parenthesis indicate the ratio of mono:di or mono:di:tri (if applicable). [d] Pd(TFA)$_2$ (5 mol%).

DIRECTED β-C(SP³)#H IODINATION AND ARYLATION OF KETONES

CROSS-REFERENCE TO RELATED APPLICATIONS

This application is a U.S. national-phase application filed under 35 U.S.C. § 371 from International Application Serial No. PCT/US2018/046465, filed on Aug. 13, 2018, and published as WO 2019/036349 on Feb. 21, 2019, which claims the benefit of priority to U.S. provisional application Ser. No. 62/546,166, filed on Aug. 16, 2017, the disclosures of each of which are incorporated by reference herein in their entireties.

STATEMENT OF GOVERNMENT LICENSE RIGHTS

This invention was made with government support under grant number GM084019 awarded by The National Institutes of Health. The government has certain rights in the invention.

BACKGROUND

Ketones are ubiquitous in organic chemistry, serving as invaluable bulk chemicals, synthetic building blocks, and natural products. While the reactivity of the α-acidic C-H bonds has been explored extensively in asymmetric enolate chemistry,[1] the direct functionalization of inert β-C(sp³)-H bonds could further expand the synthetic utility of ketones by providing new synthetic disconnections. Although stoichiometric oxime-directed β-C(sp³)-H palladation and subsequent acetoxylation and iodination have been reported since pioneering works by Shaw, Sutherland, Baldwin and others,[2] the development of corresponding catalytic reactions has remained limited in scope and efficiency despite recent advances.[3-5] Recently, the β-C(sp³)-H arylation of ketones has also been achieved using a catalytic transient amino acid directing group.[6] However, this strategy is not compatible with many synthetically desirable transformations as the free transient directing group often interferes with the coupling reagents and catalysts. Compared to the C(sp³)-H functionalization of carboxylic acids and amines, the β-C(sp³)-H functionalization of ketones using either covalent or transient directing groups has been highly limited in terms of scope of substrates as well as transformations.[7]

SUMMARY

The invention is directed, in various embodiments, to a method of β-substitution, such as β-iodination and β-arylation, of a ketone have a β-hydrogen substituent, via a Pd(II) catalyzed reaction. The method employs as a directing group an oxime of the ketone formed with an aminooxyacetic acid, followed by contact with iodine or with an aryliodide respectively. The resulting β-substituted oxime is then converted to the β-substituted ketone via cleavage of the auxiliary oxime group, such as under acidic conditions.

More specifically, the invention can provide a method of β-C(sp³)-H iodination of a ketone having a β-hydrogen substituent, comprising:

contacting the ketone and an aminooxyacetic acid in pyridine solvent to provide the corresponding oxime; then, contacting the oxime with iodine in the presence of a palladium(II) salt and phenyliodoniumacetate, in an aprotic solvent; then, hydrolyzing the oxime group under acidic conditions to provide the product β-C(sp³)-iodoketone.

For example, the aminooxyacetic acid can be aminooxyacetic acid or 2,2-dimethylaminooxyacetic acid. For example, the palladium(II) salt can be palladium(II) acetate or palladium(II)trifluoroacetate. For example, the aprotic solvent can be dioxane or 1,1,1,3,3,3-hexafluoroisopropanol. For example, the oxime group can be hydrolyzed in a solution of concentrated hydrochloric acid in dioxane.

Further, the invention can provide a method of β-C(sp³)-H arylation of a ketone having a β-hydrogen substituent, comprising:

contacting the ketone and an aminooxyacetic acid in pyridine solvent to provide the corresponding oxime; then, contacting the oxime with an aryl iodide and silver trifluoroacetate in the presence of a palladium(II) salt, in an aprotic solvent; then, hydrolyzing the oxime group under acidic conditions to provide the product β-C(sp³)-arylketone.

For example, the aminooxyacetic acid can be aminooxyacetic acid or 2,2-dimethylaminooxyacetic acid. For example, the palladium(II) salt can be palladium(II) acetate or palladium(II)trifluoroacetate. For example, the aprotic solvent can be dioxane or 1,1,1,3,3,3-hexafluoroisopropanol. For example, the oxime group can be hydrolyzed in a solution of concentrated hydrochloric acid in dioxane.

While the invention has been described and exemplified in sufficient detail for those skilled in this art to make and use it, various alternatives, modifications, and improvements will be apparent to those skilled in the art without departing from the spirit and scope of the claims.

DETAILED DESCRIPTION

Herein, we report a practical directing group that enables the β-iodination and the β-arylation of ketones. The combination of the imino-carboxylic acid chelation established in our previous transient directing group in concert with the stability of an oxime linkage successfully overcomes the limitations of previous directing groups, presumably generating a highly active Pd precursor. Consequently, The substrate scope herein reported is significantly broader than previously reported C(sp³)-H functionalizations of ketones.

Figure 1:
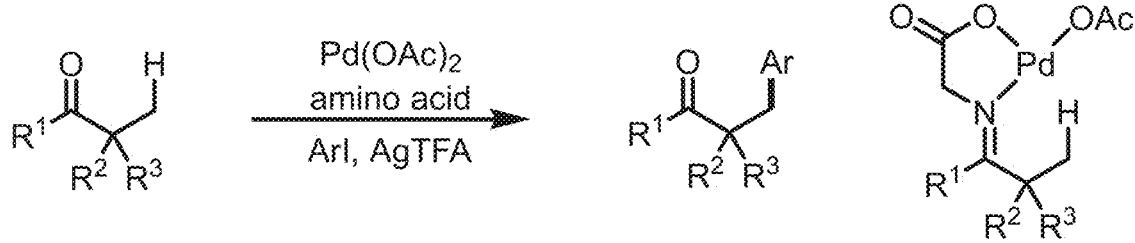
FIG. 1. Scheme 1 shows transient and covalent directing groups based on amino acids FIG. 2. Table 1. Directing group evaluation for C(sp³)-H iodination.
Figure 1:
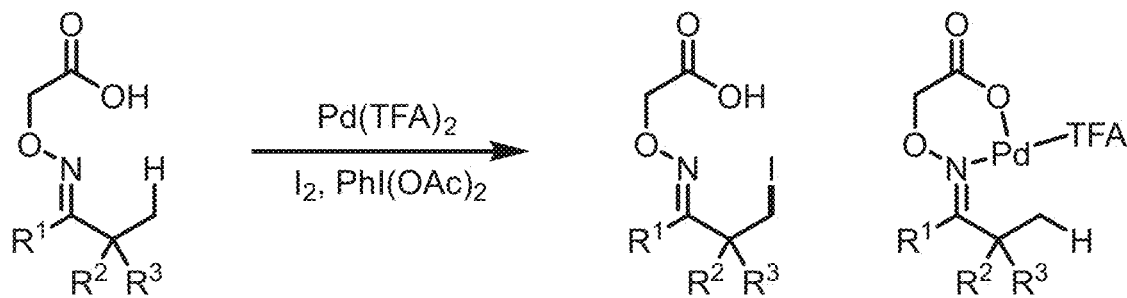

The use of amino acid transient directing groups for the β-C(sp³)-H functionalization of ketones is appealing from the viewpoint of step-economy. However, the free amino acid used is often incompatible with a range of oxidants or coupling reagents preventing the development of a diverse range of transformations. Since the bidentate imino-carboxyl chelation has been shown to be effective in directing C(sp³)-H activation,[6] we proposed to replace the imine by a more stable oxime[8] motif to render the linkage irreversible (FIG. 1; Scheme 1).

Importantly, L, X-type (i.e. neutral, anionic) directing groups have a fundamental advantage over the L, L (i.e. neutral, neutral) counterparts as shown in Scheme 2. Using L, L-type directing groups, a C—H bond must displace an acetate to form a thermodynamically unfavorable cationic Pd(II) species in order to achieve C-H insertion. (Scheme 2. Eq 2).

Furthermore, the weakly coordinating nature of the carboxylic acid is also beneficial for the reactivity of the C-H insertion intermediate compared to other highly stable bidentate complexes.

Scheme 2. Rational Design of a Powerful Directing Group

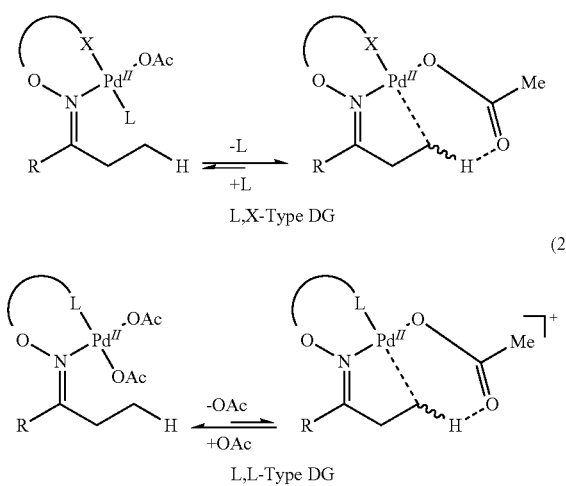

Figure 2:
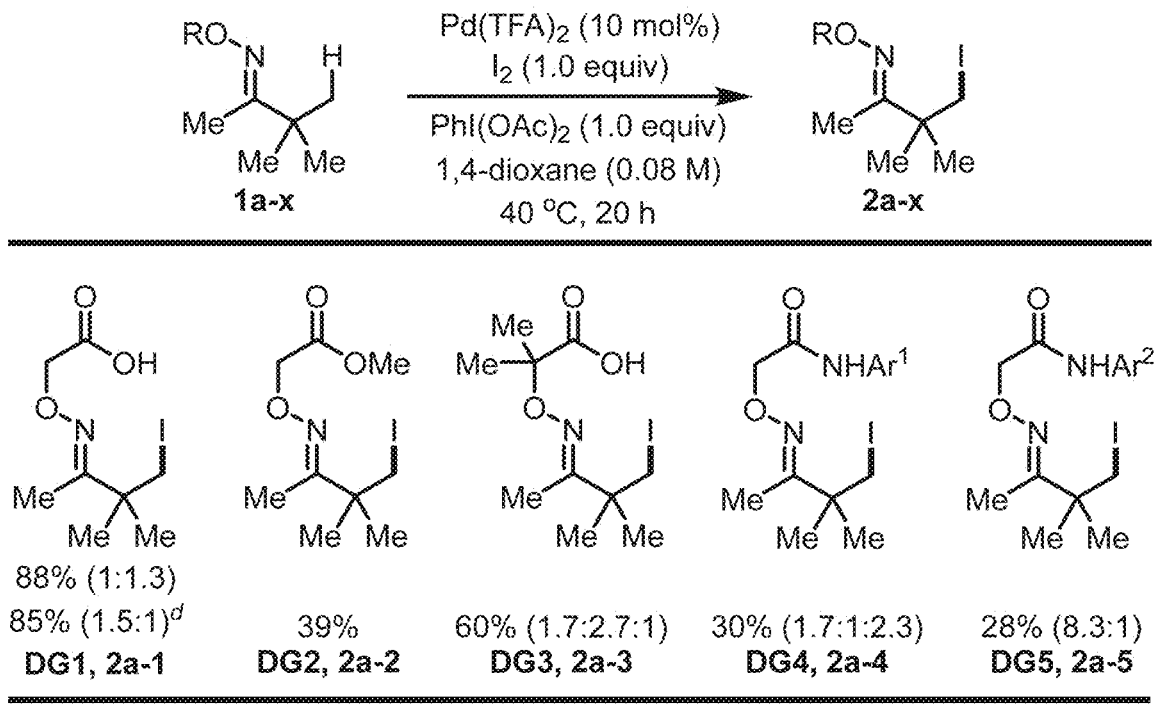

To test this design principle, we chose β-C(sp³)-H iodination as the model reaction for two reasons: First, C(sp³)-H iodination of ketones remains an unsolved problem except for a single example of stoichiometric iodination reaction of oxime reported by Sutherland in 1984.[2b] Second, β-iodoketones are extremely versatile synthons, yet the synthesis of β-iodoketones is a well-known challenge, especially for sterically hindered α-quaternary ketones.[9] Therefore, the model substrate 1a-1 was readily prepared by the condensation between pinacolone and commercially available aminooxyacetic acid under mild conditions in high yield without chromatography. Guided by our previous study of oxazoline- and acidic amide-directed β-C(sp³)-H iodination of carboxylic acid substrates,[5,10] we found that treating model substrate 1a-1 with 1 equiv I₂, PhI(OAc)₂ and 10 mol % Pd(OAc)₂ in 1,4-dioxane gave the desired iodination product in 70% yield. The use of other solvents gave significantly lower yields. Replacing Pd(OAc)₂ with Pd(TFA)₂ improved the yield to 88% (FIG. 2; Table 1).

Importantly, reducing catalyst loading to 5 mol % did not result in a noticeable decrease in yield. The observed high reactivity prompted us to investigate the coordination mode of the directing group and the impact of the structures on the reactivity. The corresponding L, L-type directing group bearing the methyl ester (DG2) gave poor yield which confirms the superiority of the L, X-type auxiliary (Scheme 2. Eq 1-2). Enhancing the bidentate coordination (due to the Thorp-Ingold effect) led to drastic increase in di- and tri-iodination products (2a-3), which is likely due to slow dissociation from Pd. Considering the well-established efficiency of the acidic amide directing group,[11] we also converted the carboxylic acid into amides (DG4 and DG5). Although DG4 has comparable reactivity, the stronger binding affinity led to predominant formation of the tri-iodinated products. As expected, the less acidic amide DG5 is not as reactive, presumably due to its inability to adopt L, X-type coordination.

With the optimal directing group and reaction conditions established, we evaluated the scope of C(sp³)-H iodination. It is worth highlighting the practical advantage of this directing group: preparation of a wide range of substrates was performed using the commercially available aminooxyacetic acid without chromatography. As shown in Table 2, a variety of alkyl substituted ketones were β-iodinated in good-to-excellent yields (2a-d). Note that the quaternary centers in products 2a-c and 2e-h are inaccessible via classic enolate alkylation methods as alkylation of the α-methyl group is kinetically favored;[1] all of these products were formed in good-to-excellent yields. The bicyclic natural product Fenchone was iodinated with excellent mono-selectivity despite the presence of three α-methyl groups (2d). Notably, aromatic moieties trans to the carboxyl directing moiety were compatible with iodination conditions and no C(sp²)-H iodination was detected (2e-g, 2o). Ketone derived from Gemfibrozil was iodinated at β-methyl group and aromatic ring (2h). Various aromatic rings cis to the carboxyl directing moiety remains intact during the iodination reaction (2i-k, 2p-r). Remarkably, no α-iodination was observed in the presence of acidic α-hydrogen,[12] only β-C(sp³)-H iodinated products were obtained (2k-m). Again, the quaternary centers in these products cannot be formed using enolate alkylation, which prefers the even more acidic and less hindered α-positions.[1] Finally, a variety of functional groups at the α-position, including nitriles, esters, TBS-protected hydroxyl, alkenyl, and alkynyl groups, were tolerated (2l-r), exhibiting significantly broader substrate scope than previously reported oxime-directed C(sp³)-H functionalizations.

TABLE 2

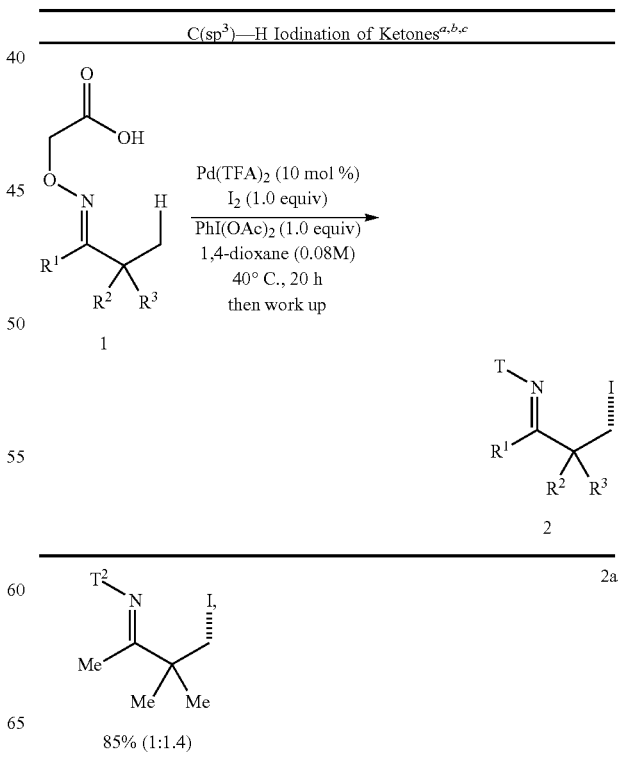

TABLE 2-continued
C(sp³)—H Iodination of Ketones[a,b,c]
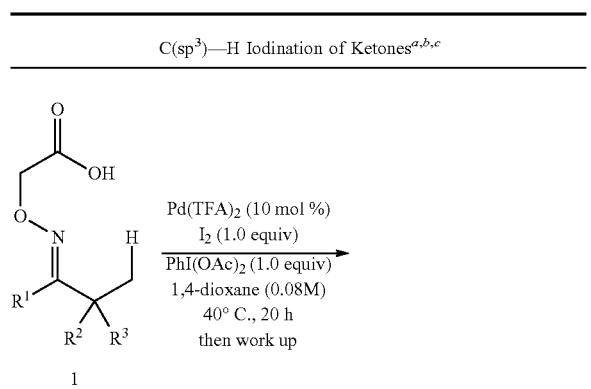
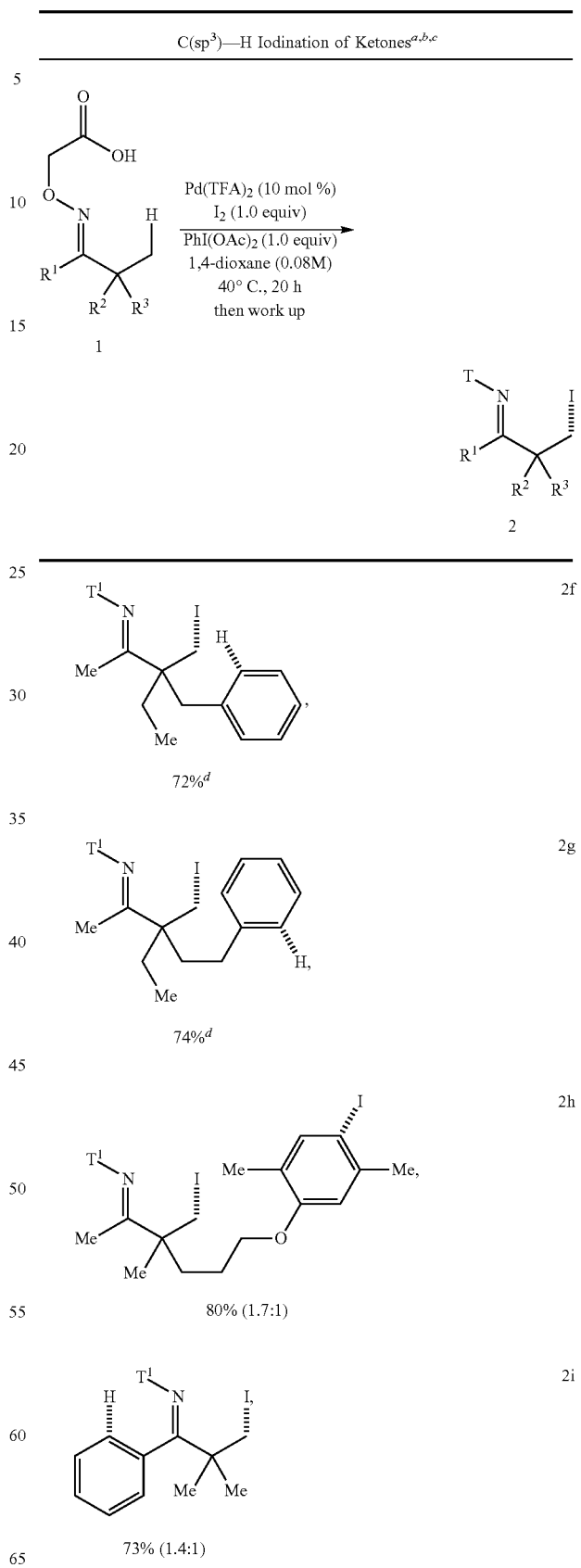

TABLE 2-continued

C(sp³)—H Iodination of Ketones[a,b,c]

[Reaction scheme: Substrate 1 with Pd(TFA)₂ (10 mol %), I₂ (1.0 equiv), PhI(OAc)₂ (1.0 equiv), 1,4-dioxane (0.08M), 40° C., 20 h, then work up → Product 2]

| Entry | Product | Yield |
|---|---|---|
| 2j | 4-MeO-C₆H₄ ketone oxime, Me, Me, CH₂I | 71% (1.4:1) |
| 2k | Ph-CH(H)- ketone oxime, Me, Me, CH₂I | 75% (1:2) |
| 2l | NC-CH(H)- ketone oxime, Me, Me, CH₂I | 50%[e] |
| 2m | EtO₂C-CH(H)- ketone oxime, Me, Me, CH₂I | 72% (3.2:1) |
| 2n | Me ketone oxime, Me, CO₂Et, CH₂I | 68% (3.9:1) |
| 2o | Me ketone oxime with CH₂-C₆H₄, CO₂Et, CH₂I | 60% |
| 2p | Ph ketone oxime, Me, OTBS, CH₂I | 65% (2.2:1)[e] |
| 2q | PhCH=CH- ketone oxime, Me, Me, CH₂I | 70% (1:1)[d] |
| 2r | PhC≡C- ketone oxime, Me, Me, CH₂I | 68% (3.2:1)[d] |

[a]Conditions: Substrate (0.1 mmol, 1.0 equiv), Pd(TFA)₂ (10 mol %), I₂(1.0 equiv), PhI(OAc)₂ (1.0 equiv), 1,4-dioxane (1.25 mL), 40° C., under air, 20 h.
[b]Isolated yield.
[c]The numbers in parenthesis indicate the ratio of mono:di.
[e]See Examples for work up procedures, T¹, and T².
[d]The reaction time is 3 h.
[e]The reaction temperature is 80° C.

This new auxiliary offers a number of practical advantages over previously developed imine directing groups.[2-5] Most importantly, imino-carboxyl directing group displayed superior reactivity over O-methyl oxime directing group with various substrates containing phenyl group, strained rings, alkenes, and other functional groups (Scheme 3).

Scheme 3. Incompatible Ketone Substrates woth O-Methyl oxime Directing Group

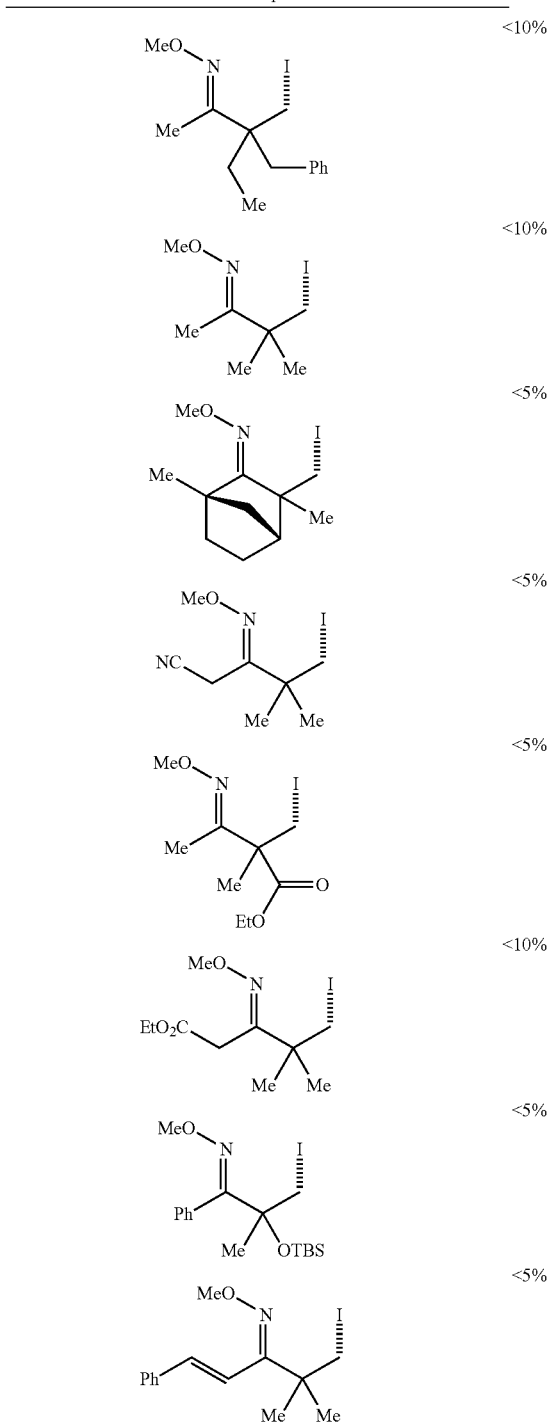

Figure 3:
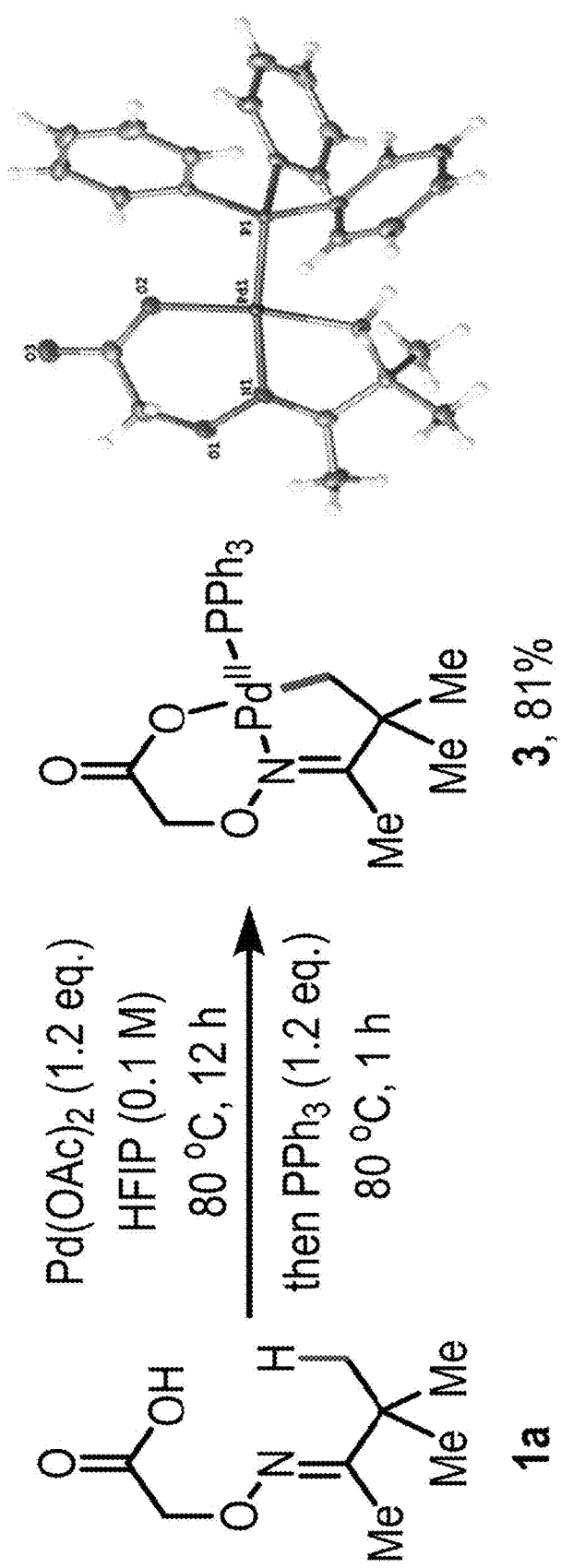
FIG. 3. Scheme 4 showing characterization of the palladacycle.

Previous attempts to isolate the C-H insertion intermediate with our previous transient amino acid directing groups were not successful due to the instability of the imine linkage. With the more stable oxime linkage, we were pleased to observe the formation of the C-H insertion intermediate by stirring the substrate 1a with 1.2 equivalents of $Pd(OAc)_2$ in HFIP at 80° C. We were able to isolate a stable complex by trapping with $PPh_3$ in 81% yield (FIG. 3; Scheme 4). The structure was confirmed by X-ray crystallography. This intermediate provides the first direct evidence for the L, X-coordination mode of the imino-carboxylic acid directing group, confirming the unique role of the carboxyl group as a directing moiety.

Scheme 5. Removal of auxiliary

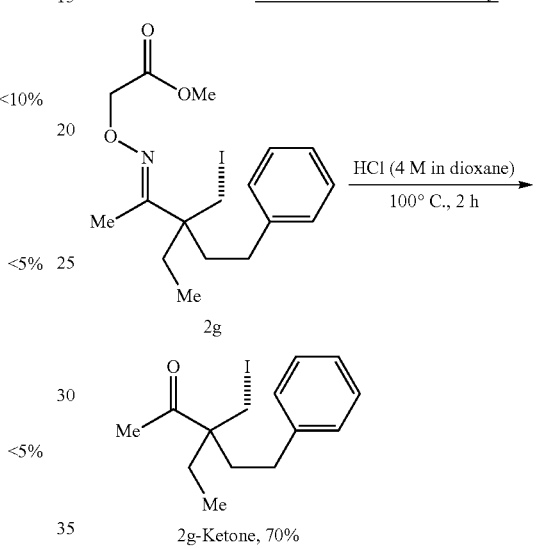

The oxime auxiliary can be cleaved following iodination using standard acid hydrolysis techniques to yield the iodinated ketone product in good yield. See the Examples section.

In summary, $C(sp^3)$-H iodination of ketones was developed using a commercially available aminooxyacetic acid auxiliary. This reaction features facile installation and removal of the auxiliary. The substrate scope is significantly broader than the previously reported C-H functionalizations of ketones using various approaches. The characterization of the C-H insertion intermediate also provides the first direct evidence for the L, X-type coordination mode of the imine-carboxylic acid directing groups.

$C(sp^3)$-H Arylation of Ketones

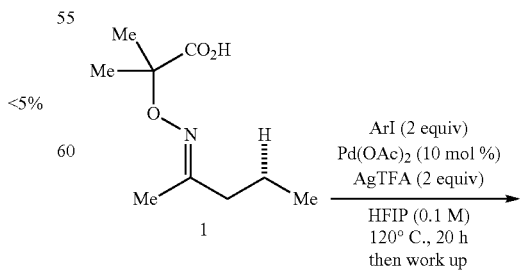

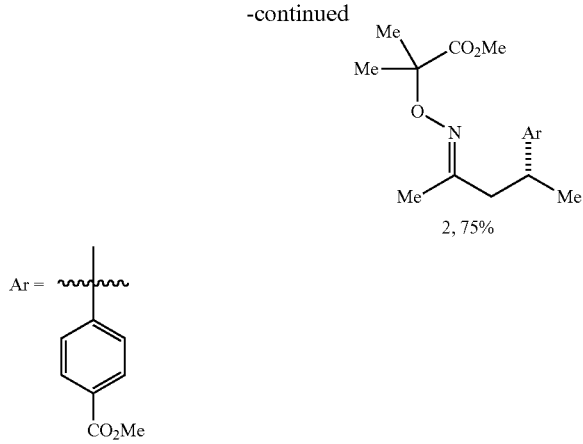

2, 75%

The new oxime directing group can also be used in the formation of β-arylketones by an analogous route. Formation of the oxime is followed by reaction with the Pd(II) salt and coupling with an aryl iodide in the presence of silver trifluoroacetate in hexafluoroisopropanol, and the resulting arylated product is worked up as before with formation of the methyl ester of the oxime carboxylic acid. Cleavage of the oxime to yield the β-arylated ketone is carried out as described above.

DOCUMENTS CITED (1) Cano, R.; Zakarian, A.; McGlacken, G. P. *Angew. Chem., Int. Ed.* 2017, DOI: 10.100²/anie.201703079.
(2) For selected examples of stoichiometric palladation reactions: (a) Constable, A. G.; McDonald, W. S.; Sawkins, L. C.; Shaw, B. L. *J. Chem. Soc. Chem, Commun.* 1978, 1061. (b) Carr, K.; Sutherland, J. K. *J. Chem. Soc. Chem, Commun.* 1984, 1227. (c) Baldwin, J. E.; Najera, C.; Yus, M. *J. Chem. Soc. Chem, Commun.* 1985, 126. (d) Baldwin, J. E.; Jones, R. H.; Najera, C.; Yus, M. *Tetrahedron* 1985, 41, 699.
(3) For early examples of Pd-catalyzed C(sp²)-H Halogenation: (a) Fahey, D. R. *J. Organomet. Chem.* 1971, 27, 283. (b) Andrienko, O. S.; Goncharov, V. S.; Raida, V. S. Russ. *J. Org. Chem.* 1996, 32, 89.
(4) For advances of catalytic C(sp³)-H activation by using oxime directing group: (a) Desai, L. V.; Hull, K. L.; Sanford, M. S. *J. Am. Chem. Soc.* 2004, 126, 9542. (b) Thu, H.-Y.; Yu, W.-Y.; Che, C.-M. *J. Am. Chem. Soc.* 2006, 128, 9048. (c) Kang, T.; Kim, Y.; Lee, D.; Wang, Z.; Chang, S. *J. Am. Chem. Soc.* 2014, 136, 4141. (d) Gao, P.; Guo, W.; Xue, J.; Zhao, Y.; Yuan, Y.; Xia, Y.; Shi, Z. *J. Am. Chem. Soc.* 2015, 137, 12231.
(5) For asymmetric C(sp³)-H iodination directed by chiral oxazoline: Giri, R.; Chen, X.; Yu. J.-Q. *Angew. Chem., Int. Ed.* 2005, 44, 2112.
(6) (a) Zhang, F.-L.; Hong, K.; Li, T.-J.; Park, H.; Yu, J.-Q. *Science* 2016, 351, 252. (b) Yang, K.; Li, Q.; Liu, Y.; Li, G.; Ge, H. *J. Am. Chem. Soc.* 2016, 138, 12775.
(7) For selected reviews on Pd-catalyzed C(sp³)-H functionalizations: (a) Daugulis, O.; Do, H.-Q.; Shabashov, D. *Acc. Chem. Res.* 2009, 42, 1074. (b) Lyons, T. W.; Sanford, M. S. *Chem. Rev.* 2010, 110, 1147. (c) He, J.; Wasa, M.; Chan, K. S. L.; Shao, Q.; Yu, J.-Q. *Chem. Rev.* 2017, DOI: 10.102¹/₀cs.chemrev.6b00622.
(8) Kalia, J.; Raines, R. T. *Angew. Chem., Int. Ed.* 2008, 47, 7523.
(9) Roman, B. I.; Kimpe, N. D.; Stevens, C. V. *Chem. Rev.* 2010, 110, 5914.
(10) For acidic amide-directed C(sp³)-H iodination: Zhu, R.-Y.; Saint-Denis, T. G.; Shao, Y.; He, J.; Sieber, J. D.; Senanayake, C. H.; Yu, J.-Q. *J. Am. Chem. Soc.* 2017, 139, 5724.
(11) For selected examples: (a) Wasa, M.; Engle, K. M.; Yu, J.-Q. *J. Am. Chem. Soc.* 2010, 132, 3680. (b) Wasa, M.; Chan, K. S. L.; Zhang, X.-G.; He, J.; Miura, M.; Yu, J.-Q. *J. Am. Chem. Soc.* 2012, 134, 18570. (c) Li, S.; Chen, G.; Feng, C.-G.; Gong, W.; Yu, J.-Q. *J. Am. Chem. Soc.* 2014, 136, 5267. (d) Zhu, R.-Y.; He, J.; Wang, X.-C.; Yu, J.-Q. *J. Am. Chem. Soc.* 2014, 136, 13194. (e) Zhu, R.-Y.; Tanaka, K.; Li, G.-C.; He, J.; Fu, H.-Y.; Li, S.-H.; Yu, J.-Q. *J. Am. Chem. Soc.* 2015, 137, 7067. (f) Wu, Q.-F.; Shen, P.-X.; He, J.; Wang, X.-B.; Zhang, F.; Shao, Q.; Zhu, R.-Y.; Mapelli, C.; Qiao, J. X.; Poss, M. A.; Yu, J.-Q. *Science* 2017, 355, 499.
(12) For selected exmaples of α-iodination for ketones: (a) Bekaert, A.; Barberan, O.; Gervais, M.; Brion, J.-D. *Tetrahedron Lett.* 2000, 41, 2903. (b) Jereb, M.; Stavber, S.; Zupan, M. *Synthesis* 2003, 853. (c) Wang, Z.; Yin, G.; Qin, J.; Gao, M.; Cao, L.; Wu, A. *Synthesis* 2008, 3565.

EXAMPLES

General Information

Ketones were obtained from the commercial sources or synthesized following literature procedures, and used to prepare the corresponding substrates. Aminooxyacetic acid hemihydrochloride was obtained from Combi-Blocks. $I_2$ was obtained from TCI. PhI(OAc)$_2$ was obtained from Sigma-Aldrich. Solvents were obtained from Sigma-Aldrich, Alfa-Aesar and Acros and used directly without further purification. Analytical thin layer chromatography was performed on 0.25 mm silica gel 60-F254. Visualization was carried out with UV light and Vogel's permanganate. $^1$H NMR was recorded on Bruker AMX-400 instrument (400 MHz) or Bruker DRX-600 instrument (600 MHz). Chemical shifts were quoted in parts per million (ppm) referenced to 0.0 ppm for tetramethylsilane. The following abbreviations (or combinations thereof) were used to explain multiplicities: s=singlet, d=doublet, t=triplet, q=quartet, m=multiplet, br=broad. Coupling constants, J, were reported in Hertz unit (Hz). $^{13}$C NMR spectra were recorded on Bruker AMX-400 instrument (100 MHz) or Bruker DRX-600 instrument (150 MHz), and were fully decoupled by broad band proton decoupling. $^{19}$F NMR spectra were recorded on Bruker AMX-400 instrument (100 MHz), and were fully decoupled by broad band proton decoupling. Chemical shifts were reported in ppm referenced to either the center line of a triplet at 77.0 ppm of chloroform-d or the center line of a multiplet at 29.84 ppm of acetone-d$^6$. In the $^{13}$C NMR analysis, peaks that correspond to those of the polyfluoroarylamide auxiliary appeared as nearly invisible, complex sets of multiplets; they were omitted in the following spectroscopic analysis. High-resolution mass spectra (HRMS) were recorded on an Agilent Mass spectrometer using ESI-TOF (electrospray ionization-time of flight).

Substrate Structures
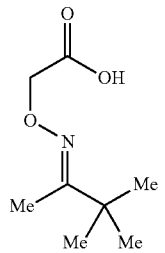
1a
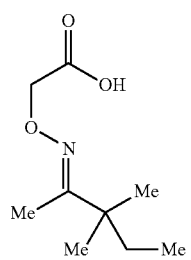
1b
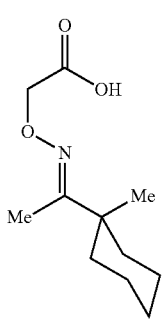
1c
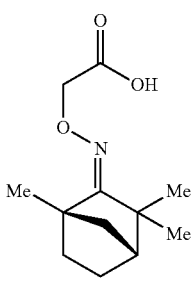
1d
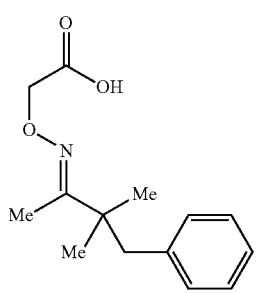
1e
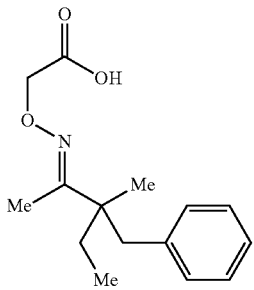
1f
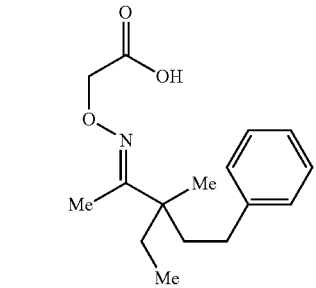
1g
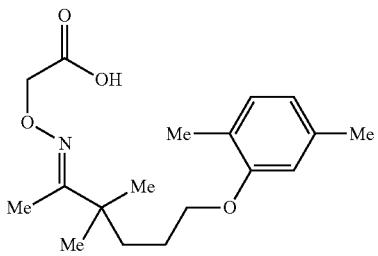
1h
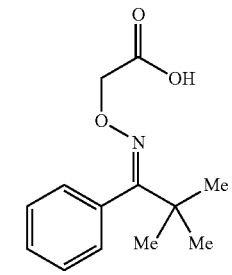
1i
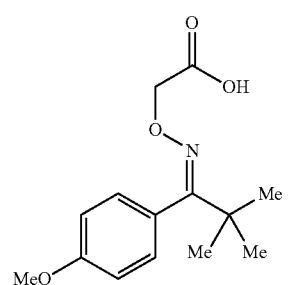
1j 1k 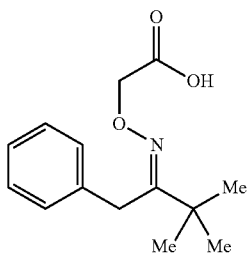

1l 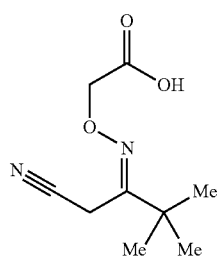

1m 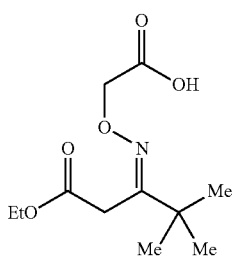

1n 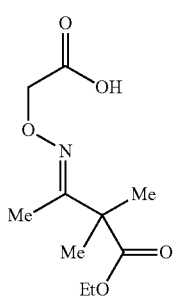

1o 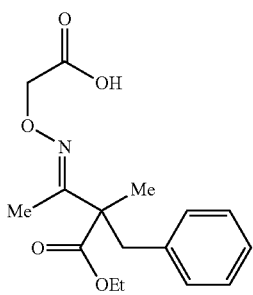

1p 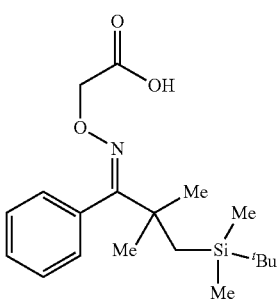

1q 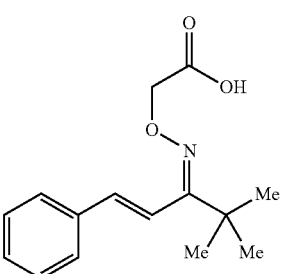

1r 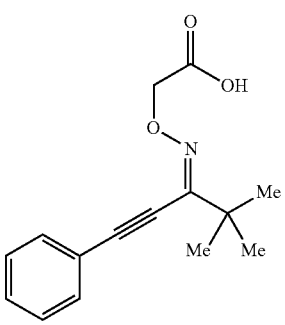

Experimental Section

Substrate Preparation

Ketones for substrates 1a, 1b, 1d, 1i, 1l, 1m and 1p are commercial available. Ketones for substrates 1e, 1f and 1g were synthesized following literature procedures.[1] Ketones for substrates 1c and 1h were synthesized by the reaction between corresponding carboxylic acids and MeLi. The procedure can be found in literature.[2] Ketone for substrate 1j was synthesized following literature procedures.[3] Ketone for substrate 1k was synthesized following literature procedures.[2] Ketones for substrates 1n and 1o were synthesized following literature procedures.[4] Ketone for substrate 1q was synthesized following literature procedures.[5] Ketone for substrate 1r was synthesized following literature procedures.[6]

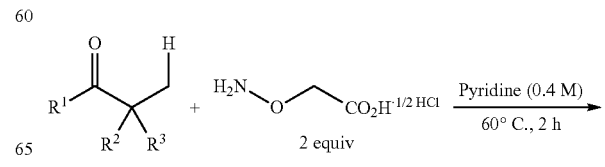

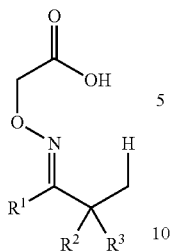

Ketone (2 mmol, 1 equiv) and aminooxyacetic acid hemihydrochloride (4 mmol, 437 mg, 2 equiv) were weighed into an oven dried 50 mL round bottom flask with a magnetic stir bar under air. 5 mL Pyridine was added and the mixture was stirred at 60° C. for 2 h. Upon completion, most pyridine was evaporated under vacuum. The resulting mixture was diluted with EtOAc (50 mL) and washed successively with water (100 mL) and diluted HCl aqueous solution (100 mL, ca. 0.01 M). The organic phase was dried with anhydrous $Na_2SO_4$ and the solvent was removed under vacuum. Notably, the pure compounds were obtained in good yields for all cases without chromatography.

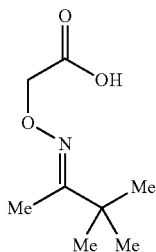 [SMILES: C/C(=N\OCC(=O)O)C(C)(C)C]

(E)-2-(((3,3-dimethylbutan-2-ylidene)amino)oxy) acetic acid (1a)

$^1$H NMR (600 MHz, $CDCl_3$) δ 4.59 (s, 2H), 1.90 (s, 3H), 1.12 (s, 9H). $^{13}$C NMR (150 MHz, $CDCl_3$) δ 174.41, 166.90, 69.93, 37.30, 27.44, 10.88. HRMS (ESI-TOF) Calcd for $C_8H_{14}NO_3^-$ [M–H]$^-$: 172.0979, found: 172.0972.

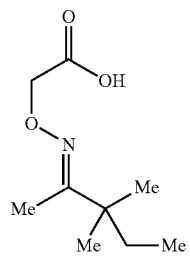

(E)-2-(((3,3-dimethylpentan-2-ylidene)amino)oxy) acetic acid (1b)

$^1$H NMR (600 MHz, $CDCl_3$) δ 4.58 (s, 2H), 1.86 (s, 3H), 1.47 (q, J=7.2 Hz, 2H), 1.08 (s, 6H), 0.76 (t, J=7.2 Hz, 3H). $^{13}$C NMR (150 MHz, $CDCl_3$) δ 174.73, 165.83, 70.05, 40.67, 32.74, 24.97, 10.79, 8.81. HRMS (ESI-TOF) Calcd for $C_9H_{16}NO_3^-$ [M–H]$^-$: 186.1136, found: 186.1132.

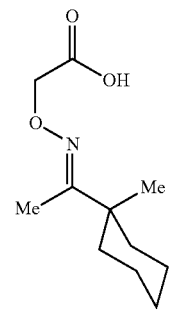

(E)-2-(((1-(1-methylcyclohexyl)ethylidene)amino) oxy)acetic acid (1c)

$^1$H NMR (600 MHz, $CDCl_3$) δ 4.60 (s, 2H), 1.88 (s, 3H), 1.82-1.79 (m, 2H), 1.51-1.31 (m, 8H), 1.07 (s, 3H). $^{13}$C NMR (150 MHz, $CDCl_3$) δ 174.06, 166.24, 69.81, 40.78, 35.20, 35.15, 26.05, 25.97, 22.35. HRMS (ESI-TOF) Calcd for $C_{11}H_{18}NO_3^-$ [M–H]$^-$: 212.1292, found: 212.1287.

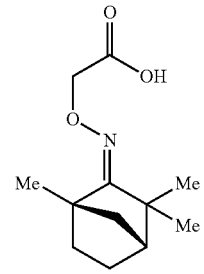

2-(((E)-((1S,4R)-1,3,3-trimethylbicyclo[2.2.1]heptan-2-ylidene)amino)oxy)acetic acid (1d)

1d was synthesized following the general procedures except the reaction temperature is 120° C. and the reaction time is 12 h. $^1$H NMR (600 MHz, $CDCl_3$) δ 4.51 (s, 2H), 1.87-1.84 (m, 1H), 1.81-1.78 (m, 1H), 1.75-1.73 (m, 1H), 1.61-1.59 (m, 2H), 1.44-1.38 (m, 2H), 1.30 (s, 3H), 1.28 (s, 3H), 1.21 (s, 3H). $^{13}$C NMR (150 MHz, $CDCl_3$) δ 176.60, 173.20, 69.98, 50.55, 48.49, 45.04, 43.31, 34.19, 25.11, 23.26, 22.47, 16.88. HRMS (ESI-TOF) Calcd for $C_{12}H_{18}NO_3^-$ [M–H]$^-$: 224.1292, found: 224.1288.

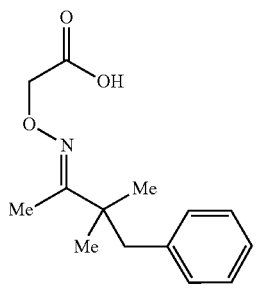 [SMILES: C/C(=N\OCC(=O)O)C(C)(C)Cc1ccccc1]

(E)-2-(((3,3-dimethyl-4-phenylbutan-2-ylidene) amino)oxy)acetic acid (1e)

$^1$H NMR (600 MHz, $CDCl_3$) δ 7.27-7.19 (m, 3H), 7.06-7.04 (m, 2H), 4.52 (s, 2H), 2.74 (s, 2H), 1.96 (s, 3H), 1.09

(s, 6H). $^{13}$C NMR (150 MHz, CDCl$_3$) δ 174.64, 165.30, 137.90, 130.26, 127.81, 126.25, 70.12, 46.05, 41.36, 25.11, 11.65. HRMS (ESI-TOF) Calcd for C$_{14}$H$_8$NO$_3^-$ [M−H]$^-$: 248.1292, found: 248.1297.

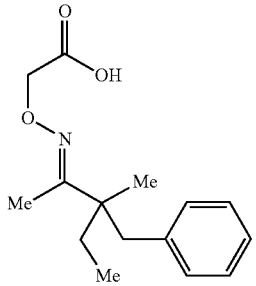 [SMILES: CCC(C)(Cc1ccccc1)/C(C)=N/OCC(=O)O]

(E)-2-(((3-benzyl-3-methylpentan-2-ylidene)amino)oxy)acetic acid (1f)

$^1$H NMR (600 MHz, CDCl$_3$) δ 7.26-7.23 (m, 2H), 7.21-7.19 (m, 1H), 7.05-7.04 (m, 2H), 4.54 (ABq, J=16.8 Hz, 2H), 2.82 (d, J=13.8 Hz, 1H), 2.67 (d, J=13.8 Hz, 1H), 1.94 (s, 3H), 1.71-1.65 (m, 1H), 1.42-1.36 (m, 1H), 0.99 (s, 3H), 0.80 (t, J=7.2 Hz, 3H). $^{13}$C NMR (150 MHz, CDCl$_3$) δ 173.94, 164.61, 137.76, 130.27, 127.83, 126.26, 70.01, 45.12, 44.97, 31.10, 20.78, 11.70, 8.64. HRMS (ESI-TOF) Calcd for C$_{15}$H$_{20}$NO$_3^-$ [M−H]$^-$: 262.1449, found: 262.1442.

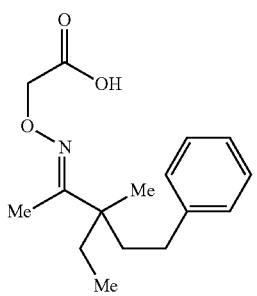

(E)-2-(((3-ethyl-3-methyl-5-phenylpentan-2-ylidene)amino)oxy)acetic acid (1g)

$^1$H NMR (600 MHz, CDCl$_3$) δ 7.28-7.25 (m, 2H), 7.18-7.14 (m, 3H), 4.63 (s, 2H), 2.52 (td, J=5.4 Hz, J=13.2 Hz, 1H), 2.38 (td, J=4.8 Hz, J=13.2 Hz, 1H), 1.86 (s, 3H), 1.83-1.78 (m, 1H), 1.66-1.54 (m, 2H), 1.47-1.41 (m, 1H), 1.12 (s, 3H), 0.78 (t, J=7.2 Hz, 3H). $^{13}$C NMR (150 MHz, CDCl$_3$) δ 174.43, 164.66, 142.62, 128.36, 128.25, 125.73, 69.89, 44.07, 41.00, 31.70, 30.77, 20.68, 10.89, 8.38. HRMS (ESI-TOF) Calcd for C$_{16}$H$_{22}$NO$_3^-$ [M−H]$^-$: 276.1605, found: 276.1609.

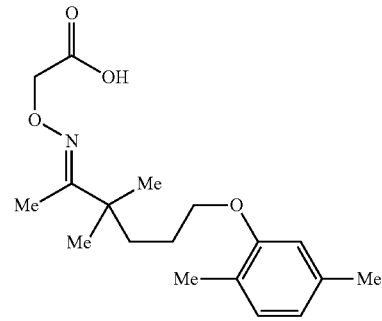 [SMILES: C/C(=N\OCC(=O)O)C(C)(C)CCCOc1cc(C)ccc1C]

(E)-2-(((6-(2,5-dimethylphenoxy)-3,3-dimethylhexan-2-ylidene)amino)oxy)acetic acid (1h)

$^1$H NMR (600 MHz, CDCl$_3$) δ 7.00 (d, J=7.2 Hz, 1H), 6.66 (d, J=7.6 Hz, 1H), 6.60 (s, 1H), 4.60 (s, 2H), 3.92-3.88 (m, 2H), 2.30 (s, 3H), 2.17 (s, 3H), 1.90 (s, 3H), 1.66-1.63 (m, 4H), 1.14 (s, 6H). $^{13}$C NMR (150 MHz, CDCl$_3$) δ 173.98, 166.02, 156.92, 136.48, 130.28, 123.48, 120.67, 111.88, 69.85, 67.78, 40.31, 36.65, 25.48, 24.78, 21.38, 15.78, 10.85. HRMS (ESI-TOF) Calcd for C$_{18}$H$_{26}$NO$_4^-$ [M−H]$^-$: 320.1867, found: 320.1862.

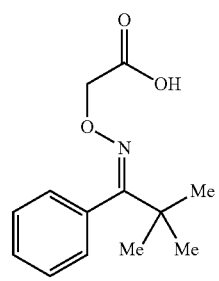 [SMILES: CC(C)(C)/C(=N/OCC(=O)O)c1ccccc1]

(Z)-2-(((2,2-dimethyl-1-phenylpropylidene)amino)oxy)acetic acid (1i)

$^1$H NMR (600 MHz, CDCl$_3$) δ 7.42-7.39 (m, 2H), 7.37-7.34 (m, 1H), 7.12-7.10 (m, 2H), 4.51 (s, 2H), 1.17 (s, 9H). $^{13}$C NMR (150 MHz, CDCl$_3$) δ 174.65, 168.26, 127.91, 127.90, 127.35, 127.34, 70.23, 37.48, 28.16. HRMS (ESI-TOF) Calcd for C$_{13}$H$_{16}$NO$_3^-$ [M−H]$^-$: 234.1136, found: 234.1130.

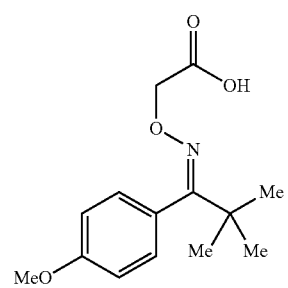 [SMILES: COc1ccc(/C(=N\OCC(=O)O)C(C)(C)C)cc1]

(Z)-2-(((1-(4-methoxyphenyl)-2,2-dimethylpropylidene)amino)oxy)acetic acid (1j)

$^1$H NMR (600 MHz, CDCl$_3$) δ 7.06-7.04 (m, 2H), 6.95-6.92 (m, 2H), 4.54 (s, 2H), 3.82 (s, 3H), 1.16 (s, 9H). $^{13}$C

NMR (150 MHz, CDCl$_3$) δ 174.14, 168.57, 159.15, 128.59, 125.62, 113.47, 70.04, 55.14, 37.71, 28.17. HRMS (ESI-TOF) Calcd for C$_{14}$H$_{18}$NO$_4$$^-$ [M−H]$^-$: 262.1241, found: 262.1247.

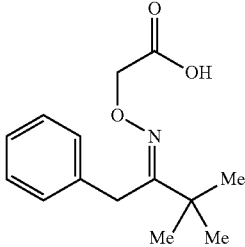 [SMILES: CC(C)(C)/C(Cc1ccccc1)=N/OCC(=O)O]

(E)-2-(((3,3-dimethyl-1-phenylbutan-2-ylidene)amino)oxy)acetic acid (1k)

$^1$H NMR (600 MHz, CDCl$_3$) δ 7.28-7.25 (m, 2H), 7.23-7.22 (m, 2H), 7.19-7.17 (m, 1H), 4.63 (s, 2H), 3.81 (s, 2H), 1.11 (s, 9H). $^{13}$C NMR (150 MHz, CDCl$_3$) δ 174.94, 167.09, 136.77, 128.43, 128.25, 126.08, 69.95, 37.81, 31.80, 28.13. HRMS (ESI-TOF) Calcd for C$_{14}$H$_{18}$NO$_3$$^-$ [M−H]$^-$: 248.1292, found: 248.1299.

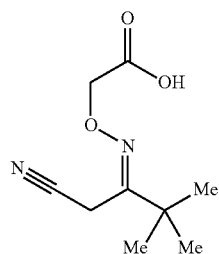

(E)-2-(((1-cyano-3,3-dimethylbutan-2-ylidene)amino)oxy)acetic acid (1l)

$^1$H NMR (600 MHz, CDCl$_3$) δ 4.75 (s, 2H), 3.36 (s, 2H), 1.19 (s, 9H). $^{13}$C NMR (150 MHz, CDCl$_3$) δ 174.19, 157.34, 115.14, 70.19, 37.46, 27.14, 13.66. HRMS (ESI-TOF) Calcd for C$_9$H$_{13}$N$_2$O$_3$$^-$ [M−H]$^-$: 197.0932, found: 197.0939.

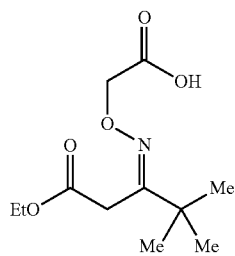 [SMILES: CCOC(=O)C/C(=N\OCC(=O)O)C(C)(C)C]

(E)-2-(((1-ethoxy-4,4-dimethyl-1-oxopentan-3-ylidene)amino)oxy)acetic acid (1m)

$^1$H NMR (600 MHz, CDCl$_3$) δ 4.64 (s, 2H), 4.21 (q, J=7.2 Hz, 2H), 3.42 (s, 2H), 1.28 (t, J=7.2 Hz, 3H), 1.12 (s, 9H).

$^{13}$C NMR (150 MHz, CDCl$_3$) δ 172.06, 170.18, 162.19, 70.92, 62.10, 37.31, 31.53, 26.96, 13.97. HRMS (ESI-TOF) Calcd for C$_{11}$H$_{18}$NO$_5$$^-$ [M−H]$^-$: 244.1190, found: 244.1185.

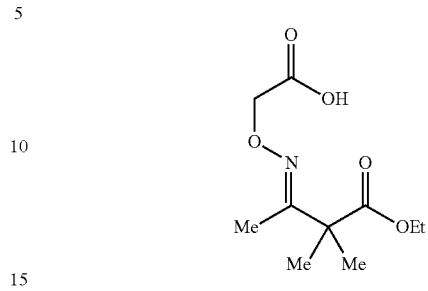

(E)-2-(((4-ethoxy-3,3-dimethyl-4-oxobutan-2-ylidene)amino)oxy)acetic acid (1n)

$^1$H NMR (400 MHz, CDCl$_3$) δ 4.65 (s, 2H), 4.16 (q, J=7.2 Hz, 2H), 1.89 (s, 3H), 1.37 (s, 6H), 1.24 (t, J=7.2 Hz, 3H). $^{13}$C NMR (150 MHz, CDCl$_3$) δ 174.70, 174.20, 161.35, 70.02, 61.17, 48.95, 23.04, 14.02, 12.46. HRMS (ESI-TOF) Calcd for C$_{10}$H$_{16}$NO$_5$$^-$ [M−H]$^-$: 230.1034, found: 230.1030.

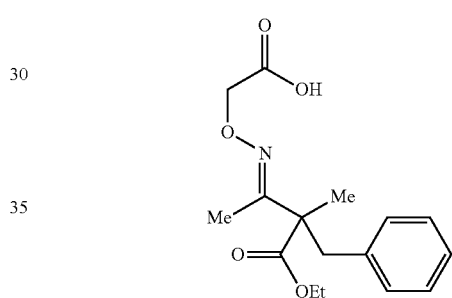

(E)-2-(((3-benzyl-4-ethoxy-3-methyl-4-oxobutan-2-ylidene)amino)oxy)acetic acid (1o)

$^1$H NMR (400 MHz, CDCl$_3$) δ 7.24-7.20 (m, 3H), 7.09-7.07 (m, 2H), 4.63 (s, 2H), 4.16 (q, J=7.2 Hz, 2H), 3.25 (d, J=13.6 Hz, 1H), 3.06 (d, J=13.6 Hz, 1H), 1.91 (s, 3H), 1.26 (s, 3H), 1.24 (t, J=8.8 Hz, 3H). $^{13}$C NMR (150 MHz, CDCl$_3$) δ 174.33, 173.60, 160.37, 136.65, 130.35, 128.01, 126.70, 70.08, 61.24, 53.82, 41.05, 20.19, 14.01, 13.30. HRMS (ESI-TOF) Calcd for C$_{16}$H$_{20}$NO$_5$$^-$ [M−H]$^-$: 306.1347, found: 306.1340.

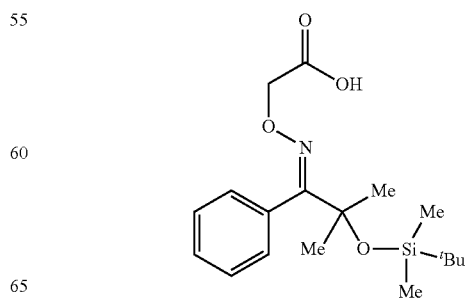

(E)-6,6,8,8,9,9-hexamethyl-5-phenyl-3,7-dioxa-4-aza-8-siladec-4-en-1-oic acid (1p)

$^1$H NMR (600 MHz, CDCl$_3$) δ 7.43-7.34 (m, 3H), 7.26-7.24 (m, 2H), 4.57 (s, 2H), 1.48 (s, 6H), 0.77 (s, 9H), 0.02 (s, 6H). $^{13}$C NMR (150 MHz, CDCl$_3$) δ 174.26, 165.76, 132.70, 128.17, 128.11, 127.65, 75.58, 70.14, 29.18, 25.75, 18.09, -2.16. HRMS (ESI-TOF) Calcd for C$_{18}$H$_{28}$NO$_4$Si$^-$ [M-H]$^-$: 350.1793, found: 350.1790.

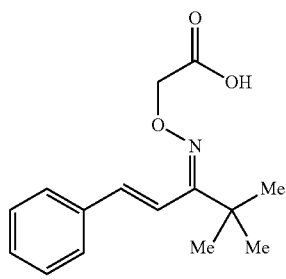 [SMILES: CC(C)(C)C(/C=C/c1ccccc1)=N/OCC(=O)O]

2-(((E)-((E)-4,4-dimethyl-1-phenylpent-1-en-3-ylidene)amino)oxy)acetic acid (1q)

$^1$H NMR (600 MHz, CDCl$_3$) δ 7.49-7.47 (m, 2H), 7.42 (d, J=16.8 Hz, 1H), 7.38-7.35 (m, 2H), 7.33-7.30 (m, 1H), 6.64 (d, J=16.8 Hz, 1H), 4.67 (s, 2H), 1.24 (s, 9H). $^{13}$C NMR (150 MHz, CDCl$_3$) δ 173.28, 163.69, 139.88, 136.47, 128.93, 128.74, 127.00, 116.29. 70.31, 37.70, 28.63. HRMS (ESI-TOF) Calcd for C$_{15}$H$_{18}$NO$_3$$^-$ [M-H]$^-$: 260.1292, found: 260.1299.

(Z)-2-(((4,4-dimethyl-1-phenylpent-1-yn-3-ylidene)amino)oxy)acetic acid (1r)

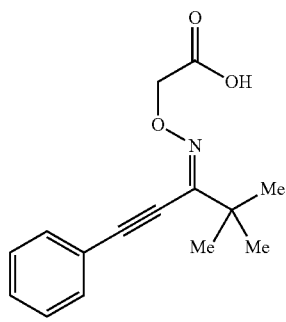 [SMILES: CC(C)(C)/C(C#Cc1ccccc1)=N/OCC(=O)O]

$^1$H NMR (600 MHz, CDCl$_3$) δ 7.54-7.52 (m, 2H), 7.39-7.34 (m, 3H), 4.72 (s, 2H), 1.26 (s, 9H). $^{13}$C NMR (150 MHz, CDCl$_3$) δ 173.92, 152.03, 132.13, 129.51, 128.40, 121.70, 101.73, 78.71, 70.52, 37.39, 28.06. HRMS (ESI-TOF) Calcd for C$_{15}$H$_{16}$NO$_3$$^-$ [M-H]$^-$: 258.1136, found: 258.1132.

C(sp$^3$)-H Iodination

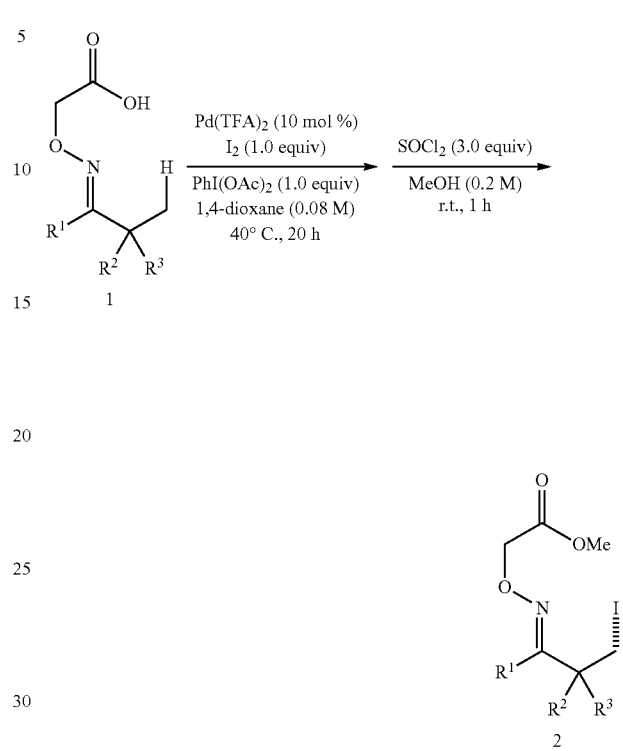

General Procedures for the C(sp$^3$)-H Iodination of UV Active Ketones: Substrate 1 (0.10 mmol), Pd(TFA)$_2$ (0.01 mmol, 3.3 mg), I$_2$ (0.10 mmol, 25.4 mg) and PhI(OAc)$_2$ (0.10 mmol, 32.2 mg) were weighed into a reaction vial (10 mL) with a magnetic stir bar under air. 1,4-Dioxane (1.25 mL) was added, and the vial was sealed with a cap. The reaction mixture was stirred at 40° C. for 20 hours. Upon completion, the reaction mixture was cooled to room temperature and diluted with EtOAc. Then the reaction mixture was filtered through a plug of silicon gel and transferred to a reaction vial (10 mL) with a magnetic stir bar. The solvent was evaporated under vacuum. Anhydrous MeOH (0.5 mL) was added to the mixture. SOCl$_2$ (0.30 mmol, 22 µL) was added dropwise at room temperature. The vial was sealed with a cap. The reaction mixture was stirred at room temperature for 1 hour. Upon completion, the reaction mixture was cooled to room temperature and the solvent was removed under vacuum. The resulting mixture was purified by preparative thin-layer chromatography.

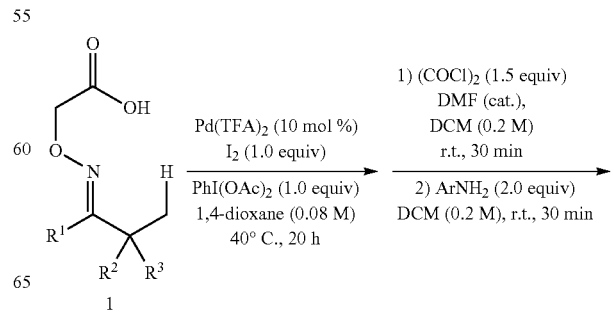

-continued

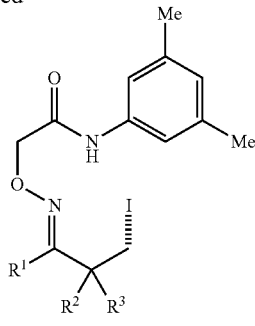

General Procedures for the C(sp³)-H Iodination of UV Inactive Ketones: Substrate 1 (0.10 mmol), Pd(TFA)₂ (0.01 mmol, 3.3 mg), $1_2$ (0.10 mmol, 25.4 mg) and PhI(OAc)₂ (0.10 mmol, 32.2 mg) were weighed into a reaction vial (10 mL) with a magnetic stir bar under air. 1,4-Dioxane (1.25 mL) was added, and the vial was sealed with a cap. The reaction mixture was stirred at 40° C. for 20 hours. Upon completion, the reaction mixture was cooled to room temperature and diluted with EtOAc. Then the reaction mixture was filtered through a plug of silicon gel and transferred to a reaction vial (10 mL) with a magnetic stir bar. The solvent was evaporated under vacuum. Anhydrous DCM (0.5 mL) and DMF (ca. 10 μL) were added to the mixture. (COCl)₂ (0.15 mmol, 13 μL) was added dropwise at room temperature. The vial was sealed with a cap. The reaction mixture was stirred at room temperature for 30 min before excess (COCl)₂ and solvent were evaporated. To the mixture was added anhydrous DCM (0.5 mL), followed by the dropwise addition of 3,5-dimethylaniline (0.2 mmol, 25 μL) to the mixture at room temperature. The vial was sealed with a cap. The reaction mixture was stirred at room temperature for 30 min. Upon completion, the reaction mixture was diluted with EtOAc. Then the reaction mixture was filtered through a plug of celite and the solvent was removed under vacuum. The resulting mixture was purified by preparative thin-layer chromatography.

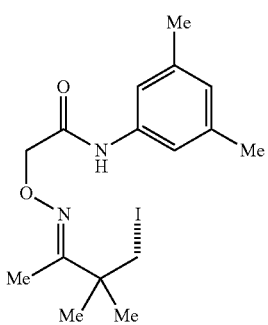

(E)-N-(3,5-dimethylphenyl)-2-(((4-iodo-3,3-dimethylbutan-2-ylidene)amino)oxy)acetamide (2a-mono)

Substrate 1a was iodinated following the general iodination procedure. After purification by preparative thin-layer chromatography (Hexane:EtOAc=5:1 as eluent), 2a-mono was obtained as a colorless oil (14.1 mg, 35%). ¹H NMR (600 MHz, CDCl₃) δ 7.86 (br s, 1H), 7.19 (s, 2H), 6.76 (s, 1H), 4.62 (s, 2H), 3.31 (s, 2H), 2.29 (s, 6H), 1.96 (s, 3H), 1.29 (s, 6H). ¹³C NMR (150 MHz, CDCl₃) δ 168.32, 163.16, 138.66, 136.98, 126.25, 117.88, 73.01, 41.14, 25.46, 21.34, 18.61, 10.85. HRMS (ESI-TOF) Calcd for C₁₆H₂₄IN₂O₂⁺ [M+H]⁺: 403.0877, found: 403.0873.

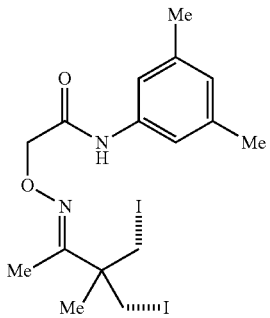

(E)-N-(3,5-dimethylphenyl)-2-(((4-iodo-3-(iodomethyl)-3-methylbutan-2-ylidene)amino)oxy)acetamide (2a-di)

Substrate 1a was iodinated following the general iodination procedure. After purification by preparative thin-layer chromatography (Hexane:EtOAc=5:1 as eluent), 2a-di was obtained as a colorless oil (26.4 mg, 50%). ¹H NMR (600 MHz, CDCl₃) δ 7.75 (br s, 1H), 7.19 (s, 2H), 6.76 (s, 1H), 4.65 (s, 2H), 3.46 (ABq, J=10.2 Hz, 4H), 2.29 (s, 6H), 2.02 (s, 3H), 1.41 (s, 3H). ¹³C NMR (150 MHz, CDCl₃) δ 167.87, 160.45, 138.67, 136.81, 126.34, 117.88, 73.21, 43.67, 23.74, 21.33, 15.46, 11.62. HRMS (ESI-TOF) Calcd for C₁₆H₂₃I₂N₂O₂⁺ [M+H]⁺: 528.9843, found: 528.9849.

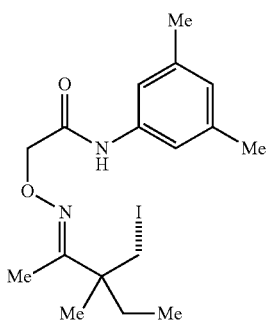

(E)-N-(3,5-dimethylphenyl)-2-(((3-(iodomethyl)-3-methylpentan-2-ylidene)amino)oxy)acetamide (2b-mono)

Substrate 1b was iodinated following the general iodination procedure. After purification by preparative thin-layer chromatography (Hexane:EtOAc=5:1 as eluent), 2b-mono was obtained as a colorless oil (12.5 mg, 30%). ¹H NMR (600 MHz, CDCl₃) δ 7.83 (br s, 1H), 7.18 (s, 2H), 6.76 (s, 1H), 4.63 (ABq, J=16.2 Hz, 2H), 3.31 (ABq, J=10.2 Hz, 2H), 2.29 (s, 6H), 1.93 (s, 3H), 1.76-1.70 (m, 1H), 1.56-1.51 (m, 1H), 1.20 (s, 3H), 0.83 (t, J=7.2 Hz, 3H). ¹³C NMR (150 MHz, CDCl₃) δ 168.33, 162.34, 138.68, 136.98, 126.24, 117.81, 73.05, 44.45, 30.46, 25.54, 22.63, 21.34, 17.88, 11.02, 9.38. HRMS (ESI-TOF) Calcd for C₁₇H₂₆IN₂O₂⁺ [M+H]⁺: 417.1033, found: 417.1029.

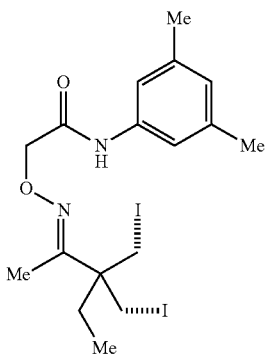

(E)-N-(3,5-dimethylphenyl)-2-(((4-iodo-3-(iodomethyl)-3-methylbutan-2-ylidene)amino)oxy)acetamide (2b-di)

Substrate 1b was iodinated following the general iodination procedure. After purification by preparative thin-layer chromatography (Hexane:EtOAc=5:1 as eluent), 2b-di was obtained as a colorless oil (29.0 mg, 55%). $^1$H NMR (600 MHz, CDCl$_3$) δ 7.72 (br s, 1H), 7.18 (s, 2H), 6.76 (s, 1H), 4.65 (s, 2H), 3.48 (ABq, J=10.8 Hz, 4H), 2.29 (s, 6H), 2.01 (s, 3H), 1.73 (q, J=7.2 Hz, 2H), 0.82 (t, J=7.2 Hz, 3H). $^{13}$C NMR (150 MHz, CDCl$_3$) δ 167.81, 159.63, 138.69, 136.78, 126.34, 117.80, 73.23, 46.91, 27.87, 21.33, 15.41, 11.84, 9.62. HRMS (ESI-TOF) Calcd for $C_{17}H_{25}I_2N_2O_2^+$ [M+H]$^+$: 543.0000, found: 543.0007.

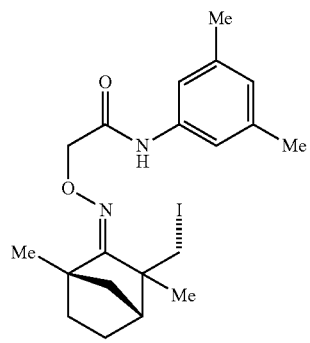

N-(3,5-dimethylphenyl)-2-(((E)-((1S,4R)-3-(iodomethyl)-1,3-dimethylbicyclo[2.2.1]heptan-2-ylidene)amino)oxy)acetamide (2d)

Substrate 1d was iodinated following the general iodination procedure except the reaction time is 3 hours and the reaction time is 3 h. After purification by preparative thin-layer chromatography (Hexane:EtOAc=5:1 as eluent), 2d was obtained as a colorless oil (19.1 mg, 42%). $^1$H NMR (600 MHz, CDCl$_3$) δ 7.84 (br s, 1H), 7.16 (s, 2H), 6.77 (s, 1H), 4.55 (s, 2H), 3.45 (ABq, J=10.2 Hz, 2H), 2.30 (s, 6H), 2.02-1.97 (m, 1H), 1.96-1.93 (m, 1H), 1.92-1.87 (m, 2H), 1.74-1.68 (m, 1H), 1.58-1.56 (m, 1H), 1.49-1.44 (m, 1H), 1.40 (s, 3H), 1.37 (s, 3H). $^{13}$C NMR (150 MHz, CDCl$_3$) δ 171.68, 168.39, 138.73, 137.07, 126.26, 117.65, 73.36, 54.54, 47.64, 45.62, 43.05, 32.19, 26.10, 23.06, 22.84, 21.39, 8.31. HRMS (ESI-TOF) Calcd for $C_{20}H_{28}IN_2O_2^+$ [M+H]$^+$: 455.1190, found: 455.1195.

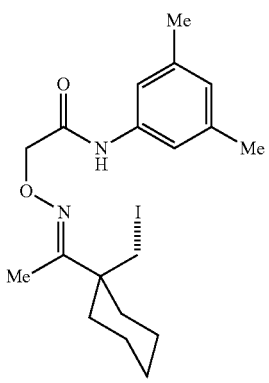

(E)-N-(3,5-dimethylphenyl)-2-(((1-(1-(iodomethyl)cyclohexyl)ethylidene)amino)oxy)acetamide (2c)

Substrate 1c was iodinated following the general iodination procedure except the reaction time is 3 hours. After purification by preparative thin-layer chromatography (Hexane:EtOAc=5:1 as eluent), 2c was obtained as a colorless oil (26.5 mg, 60%). $^1$H NMR (600 MHz, CDCl$_3$) δ 7.89 (br s, 1H), 7.20 (s, 2H), 6.75 (s, 1H), 4.64 (s, 2H), 3.29 (s, 2H), 2.29 (s, 6H), 2.02-1.99 (m, 2H), 1.91 (s, 3H), 1.53-1.31 (m, 8H). $^{13}$C NMR (150 MHz, CDCl$_3$) δ 168.46, 161.85, 138.60, 136.97, 126.21, 117.93, 73.04, 44.14, 33.77, 25.84, 22.49, 21.32, 18.20, 10.62. HRMS (ESI-TOF) Calcd for $C_{19}H_{28}IN_2O_2^+$ [M+H]$^+$: 443.1190, found: 443.1196.

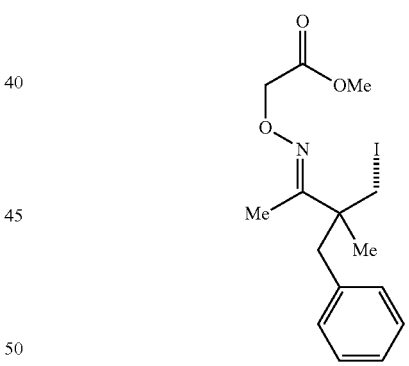

(E)-methyl 2-(((3-benzyl-4-iodo-3-methylbutan-2-ylidene)amino)oxy)acetate (2e-mono)

Substrate 1e was iodinated following the general iodination procedure. After purification by preparative thin-layer chromatography (Hexane:Acetone=20:1 as eluent), 2e-mono was obtained as a colorless oil (15.6 mg, 40%). $^1$H NMR (600 MHz, CDCl$_3$) δ 7.28-7.27 (m, 2H), 7.24-7.21 (m, 1H), 7.16-7.15 (m, 2H), 4.58 (s, 2H), 3.73 (s, 3H), 3.29 (ABq, J=10.2 Hz, 2H), 2.90 (ABq, J=13.8 Hz, 2H), 1.93 (s, 3H), 1.20 (s, 3H). $^{13}$C NMR (150 MHz, CDCl$_3$) δ 170.57, 160.68, 136.94, 130.24, 128.06, 126.61, 70.53, 51.79, 44.48, 43.28, 23.68, 17.84, 11.84. HRMS (ESI-TOF) Calcd for $C_{15}H_{21}INO_3^+$ [M+H]$^+$: 390.0561, found: 390.0555.

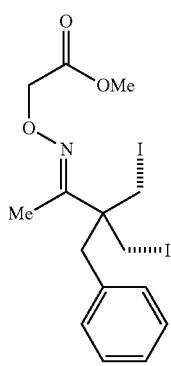

(E)-methyl 2-(((3-benzyl-4-iodo-3-(iodomethyl)butan-2-ylidene)amino)oxy)acetate (2e-di)

Substrate 1e was iodinated following the general iodination procedure. After purification by preparative thin-layer chromatography (Hexane:Acetone=20:1 as eluent), 2e-di was obtained as a colorless oil (20.6 mg, 40%). $^1$H NMR (600 MHz, CDCl$_3$) δ 7.30-7.21 (m, 5H), 4.54 (s, 2H), 3.70 (s, 3H), 3.43 (ABq, J=10.2 Hz, 4H), 2.97 (s, 2H), 2.00 (s, 3H). $^{13}$C NMR (150 MHz, CDCl$_3$) δ 170.20, 157.66, 135.89, 129.72, 128.29, 127.13, 70.74, 51.85, 47.19, 40.04, 15.86, 12.64. HRMS (ESI-TOF) Calcd for $C_{15}H_{20}I_2NO_3^+$ [M+H]$^+$: 515.9527, found: 515.9532.

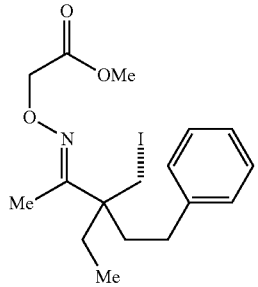

(E)-methyl 2-(((3-ethyl-3-(iodomethyl)-5-phenylpentan-2-ylidene)amino)oxy)acetate (2g)

Substrate 1g was iodinated following the general iodination procedure except the reaction time is 3 hours. After purification by preparative thin-layer chromatography (Hexane:EtOAc=5:1 as eluent), 2g was obtained as a colorless oil (30.9 mg, 74%). $^1$H NMR (600 MHz, CDCl$_3$) δ 7.29-7.27 (m, 2H), 7.20-7.17 (m, 3H), 4.64 (s, 2H), 3.73 (s, 3H), 3.50 (ABqd, J$_1$=1.2 Hz, J$_2$=10.8 Hz, 2H), 2.47 (td, J$_1$=4.8 Hz, J$_2$=13.2 Hz, 1H), 2.28 (td, J$_1$=4.8 Hz, J$_2$=13.2 Hz, 1H), 1.94 (s, 3H), 1.93-1.88 (m, 1H), 1.76-1.70 (m, 1H), 1.69-1.64 (m, 1H), 1.58-1.52 (m, 1H), 0.74 (t, J=7.2 Hz, 3H). $^{13}$C NMR (150 MHz, CDCl$_3$) δ 170.54, 159.74, 141.87, 128.42, 128.33, 125.90, 70.40, 51.76, 46.42, 38.82, 30.16, 28.97, 15.11, 11.53, 7.75. HRMS (ESI-TOF) Calcd for $C_{17}H_{25}INO_3^+$ [M+H]$^+$: 418.0874, found: 418.0880.

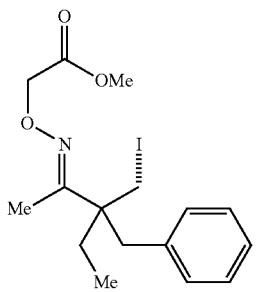

(E)-methyl 2-(((3-benzyl-3-(iodomethyl)pentan-2-ylidene)amino)oxy)acetate (2f)

Substrate 1f was iodinated following the general iodination procedure except the reaction time is 3 hours. After purification by preparative thin-layer chromatography (Hexane:EtOAc=5:1 as eluent), 2f was obtained as a colorless oil (29.0 mg, 72%). $^1$H NMR (600 MHz, CDCl$_3$) δ 7.28-7.25 (m, 2H), 7.23-7.20 (m, 3H), 4.54 (ABq, J=16.2 Hz, 2H), 3.70 (s, 3H), 3.24 (ABq, J=11.4 Hz, 2H), 2.87 (ABq, J=14.4 Hz, 2H), 1.99 (s, 3H), 1.68-1.61 (m, 2H), 0.82 (t, J=7.2 Hz, 3H). $^{13}$C NMR (150 MHz, CDCl$_3$) δ 170.52, 159.60, 136.90, 129.96, 128.10, 126.57, 70.45, 51.74, 47.73, 40.23, 28.90, 16.00, 12.31, 8.33. HRMS (ESI-TOF) Calcd for $C_{16}H_{23}INO_3^+$ [M+H]$^+$: 404.0717, found: 404.0721.

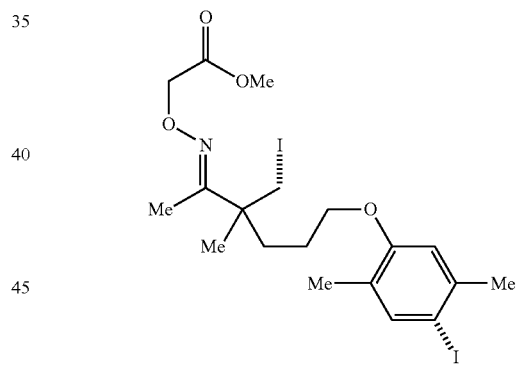

(E)-methyl 2-(((6-(4-iodo-2,5-dimethylphenoxy)-3-(iodomethyl)-3-methylhexan-2-ylidene)amino)oxy)acetate (2h-mono)

Substrate 1h was iodinated following the general iodination procedure. After purification by preparative thin-layer chromatography (Toluene:EtOAc=100:1 as eluent), 2h-mono was obtained as a colorless oil (29.4 mg, 50%). $^1$H NMR (600 MHz, CDCl$_3$) δ 7.51 (s, 1H), 6.67 (s, 1H), 4.62 (s, 2H), 3.90-3.87 (m, 2H), 3.74 (s, 3H), 3.37 (ABq, J=10.8 Hz, 2H), 2.37 (s, 3H), 2.13 (s, 3H), 1.91 (s, 3H), 1.84-1.80 (m, 1H), 1.68-1.63 (m, 3H), 1.22 (s, 3H). $^{13}$C NMR (150 MHz, CDCl$_3$) δ 170.58, 160.35, 157.27, 139.97, 139.43, 126.41, 112.58, 89.04, 70.44, 67.63, 51.76, 43.22, 34.37, 27.96, 24.59, 23.97, 18.20, 15.32, 11.12. HRMS (ESI-TOF) Calcd for $C_{19}H_{28}I_2NO_4^+$ [M+H]$^+$: 588.0102, found: 588.0106.

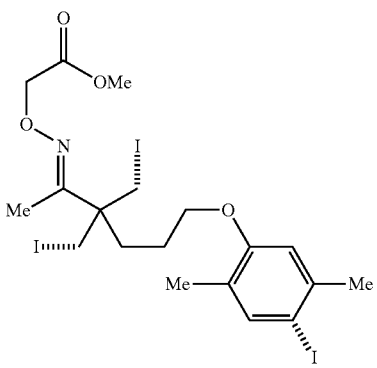

(E)-methyl 2-(((6-(4-iodo-2,5-dimethylphenoxy)-3,3-bis(iodomethyl)hexan-2-ylidene)amino)oxy)acetate (2h-di)

Substrate 1h was iodinated following the general iodination procedure. After purification by preparative thin-layer chromatography (Toluene:EtOAc=100:1 as eluent), 2h-di was obtained as a colorless oil (21.4 mg, 30%). $^1$H NMR (600 MHz, CDCl$_3$) δ 7.51 (s, 1H), 6.67 (s, 1H), 4.64 (s, 2H), 3.89 (t, J=6.0 Hz, 2H), 3.74 (s, 3H), 3.51 (ABq, J=10.8 Hz, 4H), 2.36 (s, 3H), 2.13 (s, 3H), 1.97 (s, 3H), 1.86-1.83 (m, 2H), 1.66-1.62 (m, 2H). $^{13}$C NMR (150 MHz, CDCl$_3$) δ 170.30, 157.88, 157.12, 140.02, 139.48, 126.34, 112.48, 89.17, 70.62, 67.13, 51.84, 46.02, 31.95, 27.96, 25.19, 15.96, 15.38, 11.62. HRMS (ESI-TOF) Calcd for $C_{19}H_{27}I_3NO_4^+$ [M+H]$^+$: 713.9069, found: 713.9062.

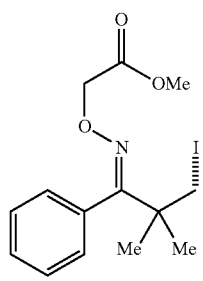

(E)-methyl 2-(((3-iodo-2-(iodomethyl)-2-methyl-1-phenylpropylidene)amino)oxy)acetate (2i-mono)

Substrate 1i was iodinated following the general iodination procedure. After purification by preparative thin-layer chromatography (Hexane:Acetone=20:1 as eluent), 2i-mono was obtained as a colorless oil (11.3 mg, 30%). $^1$H NMR (600 MHz, CDCl$_3$) δ 7.43-7.40 (m, 2H), 7.38-7.35 (m, 1H), 7.25-7.23 (m, 2H), 4.55 (s, 2H), 3.75 (s, 3H), 3.36 (s, 2H), 1.28 (s, 6H). $^{13}$C NMR (150 MHz, CDCl$_3$) δ 170.52, 162.74, 132.95, 128.25, 128.08, 127.40, 70.63, 51.74, 40.74, 26.72, 19.84. HRMS (ESI-TOF) Calcd for $C_{14}H_{19}INO_3^+$ [M+H]$^+$: 376.0404, found: 376.0400.

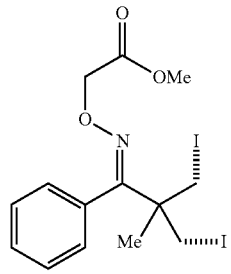

(E)-methyl 2-(((3-iodo-2-(iodomethyl)-2-methyl-1-phenylpropylidene)amino)oxy)acetate (2i-di)

Substrate 1i was iodinated following the general iodination procedure. After purification by preparative thin-layer chromatography (Hexane:Acetone=20:1 as eluent), 2i-di was obtained as a colorless oil (21.5 mg, 43%). $^1$H NMR (600 MHz, CDCl$_3$) δ 7.45-7.42 (m, 2H), 7.40-7.38 (m, 1H), 7.34-7.32 (m, 2H), 4.57 (s, 2H), 3.76 (s, 3H), 3.49 (ABq, J=10.8 Hz, 4H), 1.41 (s, 3H). $^{13}$C NMR (150 MHz, CDCl$_3$) δ 170.22, 159.30, 132.08, 128.79, 128.31, 127.38, 70.83, 51.87, 43.11, 24.88, 17.66. HRMS (ESI-TOF) Calcd for $C_{14}H_{18}I_2NO_3^+$ [M+H]$^+$: 501.9371, found: 501.9375.

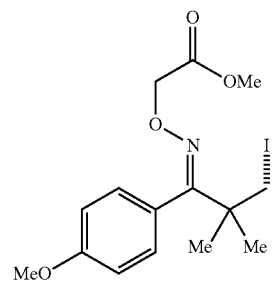

(E)-methyl 2-(((3-iodo-1-(4-methoxyphenyl)-2,2-dimethylpropylidene)amino)oxy)acetate (2j-mono)

Substrate 1j was iodinated following the general iodination procedure. After purification by preparative thin-layer chromatography (Hexane:Acetone=20:1 as eluent), 2j-mono was obtained as a colorless oil (11.7 mg, 29%). $^1$H NMR (600 MHz, CDCl$_3$) δ 7.20-7.17 (m, 2H), 6.95-6.93 (m, 2H), 4.56 (s, 2H), 3.82 (s, 3H), 3.75 (s, 3H), 3.33 (s, 2H), 1.28 (s, 6H). $^{13}$C NMR (150 MHz, CDCl$_3$) δ 170.57, 162.62, 159.33, 128.76, 124.97, 113.58, 70.61, 55.15, 51.73, 40.92, 26.70, 20.02. HRMS (ESI-TOF) Calcd for $C_{15}H_{21}INO_4^+$ [M+H]$^+$: 406.0510, found: 406.0515.

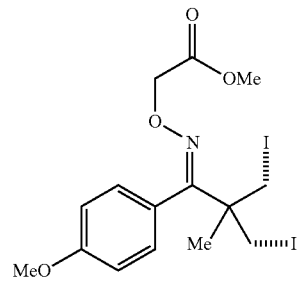

(E)-methyl 2-(((3-iodo-2-(iodomethyl)-1-(4-methoxyphenyl)-2-methylpropylidene)amino)oxy)acetate (2j-di)

Substrate 1j was iodinated following the general iodination procedure. After purification by preparative thin-layer chromatography (Hexane:Acetone=20:1 as eluent), 2j-di was obtained as a colorless oil (22.3 mg, 42%). $^1$H NMR (600 MHz, CDCl$_3$) δ 7.28-7.26 (m, 2H), 6.97-6.94 (m, 2H), 4.57 (s, 2H), 3.82 (s, 3H), 3.76 (s, 3H), 3.48 (ABq, J=10.8 Hz, 4H), 1.41 (s, 3H). $^{13}$C NMR (150 MHz, CDCl$_3$) δ 170.27, 159.72, 159.26, 128.79, 124.04, 113.76, 70.80, 55.18, 51.85, 43.30, 24.84, 17.79. HRMS (ESI-TOF) Calcd for C$_{15}$H$_{20}$I$_2$NO$_4^+$ [M+H]$^+$: 531.9476, found: 531.9471.

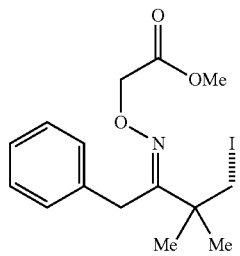

(E)-methyl 2-(((4-iodo-3,3-dimethyl-1-phenylbutan-2-ylidene)amino)oxy)acetate (2k-mono)

Substrate 1k was iodinated following the general iodination procedure. After purification by preparative thin-layer chromatography (Hexane:Acetone=10:1 as eluent), 2k-mono was obtained as a colorless oil (9.7 mg, 25%). $^1$H NMR (600 MHz, CDCl$_3$) δ 7.30-7.27 (m, 4H), 7.22-7.18 (m, 1H), 4.66 (s, 2H), 3.82 (s, 2H), 3.78 (s, 3H), 3.34 (s, 2H), 1.18 (s, 6H). $^{13}$C NMR (150 MHz, CDCl$_3$) δ 170.56, 161.85, 136.30, 128.52, 128.47, 126.23, 70.58, 51.81, 40.89, 31.78, 26.69, 20.17. HRMS (ESI-TOF) Calcd for C$_{15}$H$_{21}$INO$_3^+$ [M+H]$^+$: 390.0561, found: 390.0569.

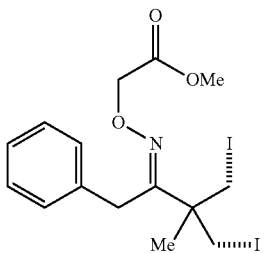

(E)-methyl 2-(((4-iodo-3-(iodomethyl)-3-methyl-1-phenylbutan-2-ylidene)amino)oxy)acetate (2k-di)

Substrate 1k was iodinated following the general iodination procedure. After purification by preparative thin-layer chromatography (Hexane:Acetone=10:1 as eluent), 2k-di was obtained as a colorless oil (25.8 mg, 50%). $^1$H NMR (600 MHz, CDCl$_3$) δ 7.30-7.29 (m, 4H), 7.24-7.20 (m, 1H), 4.70 (s, 2H), 3.85 (s, 2H), 3.79 (s, 3H), 3.45 (ABq, J=10.2 Hz, 4H), 1.28 (s, 3H). $^{13}$C NMR (150 MHz, CDCl$_3$) δ 170.24, 158.72, 135.61, 128.64, 126.56, 70.82, 51.92, 43.41, 32.11, 24.85, 17.74. HRMS (ESI-TOF) Calcd for C$_{15}$H$_{20}$I$_2$NO$_3^+$ [M+H]$^+$: 515.9527, found: 515.9520.

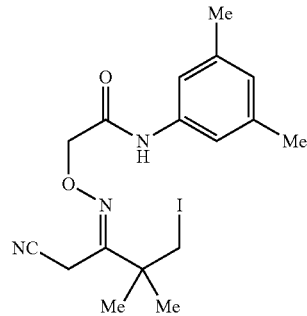 [SMILES: Cc1cc(C)cc(NC(=O)CO/N=C(\CC#N)C(C)(C)CI)c1]

(E)-2-(((1-cyano-4-iodo-3,3-dimethylbutan-2-ylidene)amino)oxy)-N-(3,5-dimethylphenyl)acetamide (2l)

Substrate 1l was iodinated following the general iodination procedure except the reaction temperature is 80° C. After purification by preparative thin-layer chromatography (Hexane: EtOAc=2:1 as eluent), 2l was obtained as a colorless oil (21.4 mg, 50%). $^1$H NMR (600 MHz, CDCl$_3$) δ 8.06 (br s, 1H), 7.28 (s, 2H), 6.76 (s, 1H), 4.81 (s, 2H), 3.35 (s, 2H), 3.29 (s, 2H), 2.29 (s, 6H), 1.36 (s, 6H). $^{13}$C NMR (150 MHz, CDCl$_3$) δ 166.71, 154.24, 138.61, 137.06, 126.33, 117.78, 115.38, 74.28, 41.36, 25.44, 21.36, 15.99, 14.26. HRMS (ESI-TOF) Calcd for C$_{17}$H$_{23}$IN$_3$O$_2^+$ [M+H]$^+$: 428.0829, found: 428.0822.

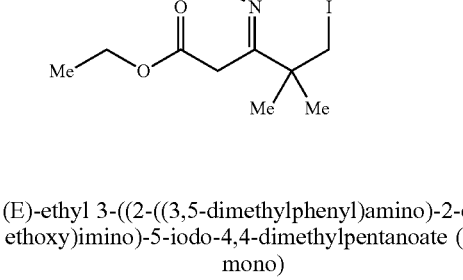

(E)-ethyl 3-((2-((3,5-dimethylphenyl)amino)-2-oxoethoxy)imino)-5-iodo-4,4-dimethylpentanoate (2m-mono)

Substrate 1m was iodinated following the general iodination procedure. After purification by preparative thin-layer chromatography (Hexane:EtOAc=5:1 as eluent), the iodinated products were obtained as 3.4:1 (mono:di) inseparable mixtures (2m-mono, 26.1 mg, 55%). $^1$H NMR (600 MHz, CDCl$_3$) δ 8.63 (br s, 1H), 7.40 (s, 2H), 6.75 (s, 1H), 4.68 (s, 2H), 4.24 (q, J=7.2 Hz, 2H), 3.42 (s, 2H), 3.31 (s, 2H), 2.30 (s, 6H), 1.30 (t, J=7.2 Hz, 3H), 1.28 (s, 6H). $^{13}$C NMR (150 MHz, CDCl$_3$) δ 169.29, 168.21, 157.74, 138.34, 137.86, 125.83, 117.73, 73.51, 61.83, 40.63, 31.77, 25.58, 21.43, 17.59, 14.04. HRMS (ESI-TOF) Calcd for C$_{19}$H$_{28}$IN$_2$O$_4^+$ [M+H]$^+$: 475.1088, found: 475.1084.

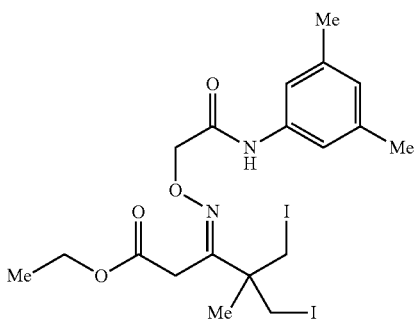 [SMILES: CCOC(=O)C/C(=N\OCC(=O)Nc1cc(C)cc(C)c1)C(C)(CI)CI]

(E)-ethyl 3-((2-((3,5-dimethylphenyl)amino)-2-oxo-ethoxy)imino)-5-iodo-4-(iodomethyl)-4-methylpentanoate (2m-di)

Substrate 1m was iodinated following the general iodination procedure. After purification by preparative thin-layer chromatography (Hexane:EtOAc=5:1 as eluent), the iodinated products were obtained as 3.4:1 (mono:di) inseparable mixtures (2m-di, 10.2 mg, 17%). $^1$H NMR (600 MHz, CDCl$_3$) δ 8.60 (br s, 1H), 7.40 (s, 2H), 6.75 (s, 1H), 4.71 (s, 2H), 4.25 (q, J=7.2 Hz, 2H), 3.47 (s, 2H), 3.46 (ABq, J=10.8 Hz, 4H), 2.30 (s, 6H), 1.42 (s, 3H), 1.31 (t, J=7.2 Hz, 3H). $^{13}$C NMR (150 MHz, CDCl$_3$) δ 168.80, 167.79, 154.89, 138.36, 137.76, 125.91, 117.72, 73.80, 62.06, 43.30, 32.34, 29.44, 24.00, 17.60, 15.43. HRMS (ESI-TOF) Calcd for C$_{19}$H$_{27}$I$_2$N$_2$O$_4^+$ [M+H]$^+$: 601.0055, found: 601.0051.

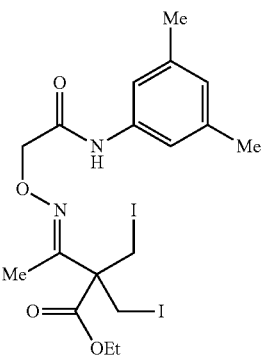

(E)-ethyl 3-((2-((3,5-dimethylphenyl)amino)-2-oxo-ethoxy)imino)-2,2-bis(iodomethyl)butanoate (2n-di)

Substrate 1n was iodinated following the general iodination procedure. After purification by preparative thin-layer chromatography (Hexane:EtOAc=5:1 as eluent), the iodinated products were obtained as 4.0:1 (mono:di) inseparable mixtures (2n-di, 8.2 mg, 14%). $^1$H NMR (600 MHz, CDCl$_3$) δ 7.68 (br s, 1H), 7.18 (s, 2H), 6.77 (s, 1H), 4.70 (s, 2H), 4.28-4.17 (m, 2H), 3.78 (ABq, J=9.6 Hz, 4H), 2.29 (s, 6H), 1.98 (s, 3H), 1.31 (t, J=7.2 Hz, 3H). $^{13}$C NMR of mixture (150 MHz, CDCl$_3$) δ 170.70, 167.78, 167.42, 167.16, 158.93, 156.69, 138.71, 138.70, 136.87, 136.72, 126.43, 126.34, 117.83, 117.76, 73.49, 73.27, 62.96, 62.05, 56.71, 53.06, 22.05, 21.32, 14.12, 14.08, 12.74, 12.64, 11.48, 10.59. HRMS (ESI-TOF) Calcd for C$_{18}$H$_{25}$I$_2$N$_2$O$_4^+$ [M+H]$^+$: 586.9898, found: 586.9891.

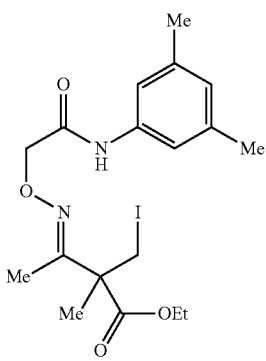 [SMILES: CCOC(=O)C(C)(CI)/C(C)=N/OCC(=O)Nc1cc(C)cc(C)c1]

(E)-ethyl 3-((2-((3,5-dimethylphenyl)amino)-2-oxo-ethoxy)imino)-2-(iodomethyl)-2-methylbutanoate (2n-mono)

Substrate 1n was iodinated following the general iodination procedure. After purification by preparative thin-layer chromatography (Hexane:EtOAc=5:1 as eluent), the iodinated products were obtained as 4.0:1 (mono:di) inseparable mixtures (2n-mono, 24.8 mg, 54%). $^1$H NMR (600 MHz, CDCl$_3$) δ 7.75 (br s, 1H), 7.18 (s, 2H), 6.77 (s, 1H), 4.66 (ABq, J=16.2 Hz, 2H), 4.28-4.17 (m, 2H), 3.59 (ABq, J=10.2 Hz, 2H), 2.30 (s, 6H), 1.97 (s, 3H), 1.50 (s, 3H), 1.27 (t, J=7.2 Hz, 3H). $^{13}$C NMR of mixture (150 MHz, CDCl$_3$) δ 170.70, 167.78, 167.42, 167.16, 158.93, 156.69, 138.71, 138.70, 136.87, 136.72, 126.43, 126.34, 117.83, 117.76, 73.49, 73.27, 62.96, 62.05, 56.71, 53.06, 22.05, 21.32, 14.12, 14.08, 12.74, 12.64, 11.48, 10.59. HRMS (ESI-TOF) Calcd for C$_{18}$H$_{26}$IN$_2$O$_4^+$ [M+H]$^+$: 461.0932, found: 461.0939.

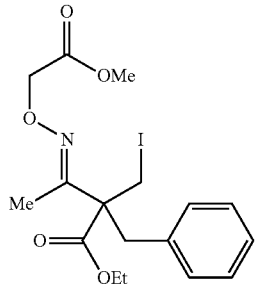 [SMILES: CCOC(=O)C(CI)(Cc1ccccc1)/C(C)=N/OCC(=O)OC]

(E)-ethyl 2-benzyl-2-(iodomethyl)-3-((2-methoxy-2-oxoethoxy)imino)butanoate (2o)

Substrate 1o was iodinated following the general iodination procedure. After purification by preparative thin-layer chromatography (Hexane:EtOAc=5:1 as eluent), 2o was obtained as 1.6:1 (2o: starting material) inseparable mixture (32.2 mg, 60%). $^1$H NMR (600 MHz, CDCl$_3$) δ 7.28-7.18 (m, 4H), 7.11-7.09 (m, 1H), 4.57 (ABq, J=16.2 Hz, 2H), 4.27-4.18 (m, 2H), 3.73 (s, 3H), 3.41 (ABq, J=11.4 Hz, 2H), 3.28 (ABq, J=14.4 Hz, 2H), 1.93 (s, 3H), 1.28 (t, J=7.2 Hz, 3H). $^{13}$C NMR of mixture (150 MHz, CDCl$_3$) δ 173.68, 170.47, 170.17, 170.13, 156.45, 136.99, 135.64, 130.42, 130.04, 128.26, 128.23, 127.94, 127.02, 126.53, 70.74, 61.94, 61.06, 57.50, 53.74, 51.82, 51.73, 41.10, 37.69, 20.25, 14.07, 14.03, 16.34, 13.13, 9.90. HRMS (ESI-TOF) Calcd for C$_{24}$H$_{30}$IN$_2$O$_4^+$ [M+H]$^+$: 537.1245, found: 537.1240.

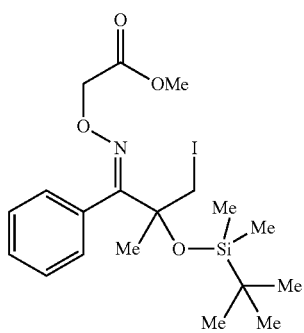 [SMILES: COC(=O)CO/N=C(\c1ccccc1)C(C)(CI)O[Si](C)(C)C(C)(C)C]

(E)-methyl 6-(iodomethyl)-6,8,8,9,9-pentamethyl-5-phenyl-3,7-dioxa-4-aza-8-siladec-4-en-1-oate (2p-mono)

Substrate 1p was iodinated following the general iodination procedure except the reaction temperature is 80° C. After purification by preparative thin-layer chromatography (Toluene:EtOAc=100:1 as eluent), 2p-mono was obtained as a colorless oil (22.1 mg, 45%). $^1$H NMR (600 MHz, CDCl$_3$) δ 7.40-7.34 (m, 5H), 4.58 (s, 2H), 3.76 (s, 3H), 3.42 (ABq, J=9.6 Hz, 2H), 1.68 (s, 3H), 0.80 (s, 9H), 0.14 (s, 3H), 0.01 (s, 3H). $^{13}$C NMR (150 MHz, CDCl$_3$) δ 170.42, 161.17, 131.92, 128.45, 128.22, 127.78, 76.40, 70.82, 51.81, 27.11, 25.89, 18.37, 17.86, −1.80, −2.48. HRMS (ESI-TOF) Calcd for C$_{19}$H$_{31}$INO$_4$Si$^+$ [M+H]$^+$: 492.1062, found: 492.1066.

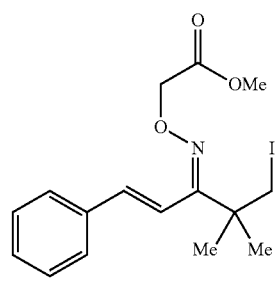

methyl 2-(((E)-((E)-5-iodo-4,4-dimethyl-1-phenyl-pent-1-en-3-ylidene)amino)oxy)acetate (2q-mono)

Substrate 1q was iodinated following the general iodination procedure. After purification by preparative thin-layer chromatography (Hexane:Acetone=20:1 as eluent), 2q-mono was obtained as a colorless oil (14.0 mg, 35%). $^1$H NMR (600 MHz, CDCl$_3$) δ 7.49-7.46 (m, 2H), 7.42 (d, J=16.8 Hz, 1H), 7.37-7.34 (m, 2H), 7.32-7.29 (m, 1H), 6.56 (d, J=16.8 Hz, 1H), 4.68 (s, 2H), 3.78 (s, 3H), 3.41 (s, 2H), 1.36 (s, 6H). $^{13}$C NMR (150 MHz, CDCl$_3$) δ 170.43, 158.24, 139.42, 136.52, 128.80, 128.69, 126.99, 116.05, 71.00, 51.86, 40.72, 26.84, 20.24. HRMS (ESI-TOF) Calcd for C$_{16}$H$_{21}$INO$_3^+$ [M+H]$^+$: 402.0561, found: 402.0555.

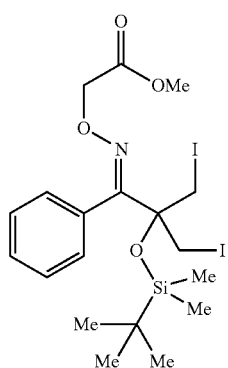 [SMILES: COC(=O)CO/N=C(\c1ccccc1)C(CI)(CI)O[Si](C)(C)C(C)(C)C]

(E)-methyl 6,6-bis(iodomethyl)-8,8,9,9-tetramethyl-5-phenyl-3,7-dioxa-4-aza-8-siladec-4-en-1-oate (2p-di)

Substrate 1p was iodinated following the general iodination procedure except the reaction temperature is 80° C. After purification by preparative thin-layer chromatography (Toluene:EtOAc=100:1 as eluent), 2p-di was obtained as a colorless oil (12.3 mg, 20%). $^1$H NMR (600 MHz, CDCl$_3$) δ 7.46-7.44 (m, 2H), 7.42-7.38 (m, 3H), 4.63 (s, 2H), 3.78 (s, 3H), 3.69 (ABq, J=10.2 Hz, 4H), 0.92 (s, 9H), 0.15 (s, 6H). $^{13}$C NMR (150 MHz, CDCl$_3$) δ 170.05, 156.26, 130.90, 129.13, 128.42, 128.02, 76.21, 71.10, 51.98, 26.02, 18.68, 15.86, −2.14. HRMS (ESI-TOF) Calcd for C$_{19}$H$_{30}$I$_2$NO$_4$Si$^+$ [M+H]$^+$: 618.0028, found: 618.0020.

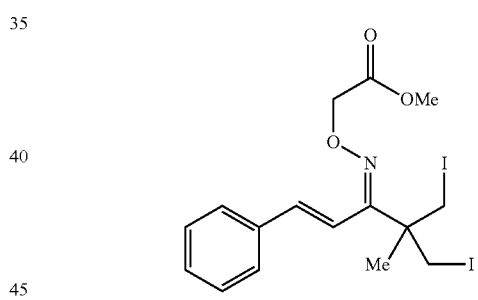

methyl 2-(((E)-((E)-5-iodo-4-(iodomethyl)-4-methyl-1-phenylpent-1-en-3-ylidene)amino)oxy)acetate (2q-di)

Substrate 1q was iodinated following the general iodination procedure. After purification by preparative thin-layer chromatography (Hexane:EtOAc=20:1 as eluent), 2q-di was obtained as a colorless oil (18.4 mg, 35%). $^1$H NMR (600 MHz, CDCl$_3$) δ 7.49-7.47 (m, 2H), 7.42 (d, J=16.8 Hz, 1H), 7.38-7.36 (m, 2H), 7.33-7.31 (m, 1H), 6.49 (d, J=16.8 Hz, 1H), 4.69 (s, 2H), 3.79 (s, 3H), 3.55 (ABq, J=10.2 Hz, 4H), 1.52 (s, 3H). $^{13}$C NMR (150 MHz, CDCl$_3$) δ 170.16, 155.74, 140.17, 136.13, 129.06, 128.74, 127.08, 115.43, 71.17, 51.96, 43.13, 24.92, 17.60. HRMS (ESI-TOF) Calcd for C$_{16}$H$_{20}$I$_2$NO$_3^+$ [M+H]$^+$: 527.9527, found: 527.9521.

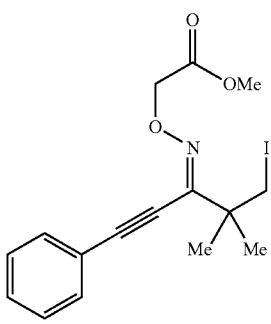 [SMILES: COC(=O)CO/N=C(\C#Cc1ccccc1)C(C)(C)CI]

(E)-methyl 2-(((5-iodo-4,4-dimethyl-1-phenylpent-1-yn-3-ylidene)amino)oxy)acetate (2r-mono)

Substrate 1r was iodinated following the general iodination procedure. After purification by preparative thin-layer chromatography (Hexane:EtOAc=10:1 as eluent), the iodinated products were obtained as 1.9:1 (mono:di) inseparable mixtures (2r-mono, 20.7 mg, 52%). $^1$H NMR (600 MHz, CDCl$_3$) δ 7.55-7.53 (m, 2H), 7.38-7.34 (m, 3H), 4.73 (s, 2H), 3.78 (s, 3H), 3.45 (s, 2H), 1.39 (s, 6H). $^{13}$C NMR (150 MHz, CDCl$_3$) δ 169.70, 146.92, 132.15, 129.59, 128.40, 121.55, 101.62, 78.23, 71.19, 51.92, 40.46, 26.18, 16.11. HRMS (ESI-TOF) Calcd for $C_{16}H_{19}INO_3^+$ [M+H]$^+$: 400.0404, found: 400.0400.

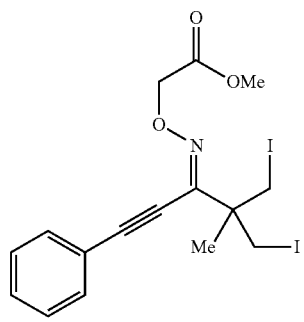 [SMILES: COC(=O)CO/N=C(\C#Cc1ccccc1)C(C)(CI)CI]

(E)-methyl 2-(((3-iodo-2-(iodomethyl)-2-methyl-1-phenylpropylidene)amino)oxy)acetate (2r-di)

Substrate 1r was iodinated following the general iodination procedure. After purification by preparative thin-layer chromatography (Hexane:EtOAc=10:1 as eluent), the iodinated products were obtained as 1.9:1 (mono:di) inseparable mixtures (2r-di, 8.4 mg, 16%). $^1$H NMR (600 MHz, CDCl$_3$) δ 7.56-7.54 (m, 2H), 7.43-7.39 (m, 3H), 4.75 (s, 2H), 3.79 (s, 3H), 3.59 (ABq, J=10.2 Hz, 4H), 1.54 (s, 3H). $^{13}$C NMR (150 MHz, CDCl$_3$) δ 169.96, 143.74, 132.21, 129.87, 128.47, 121.15, 102.03, 77.69, 71.39, 52.02, 42.89, 24.71, 18.97. HRMS (ESI-TOF) Calcd for $C_{16}H_{18}I_2NO_3^+$ [M+H]$^+$: 525.9371, found: 525.9377.

The Synthesis and Characterization of Palladacycle

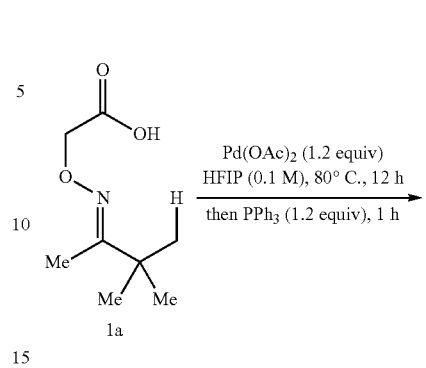

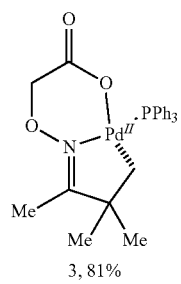

3, 81%

The General Procedures for the Palladacycle Synthesis: Substrate 1a (0.1 mmol, 17.3 mg) and Pd(OAc)$_2$ (0.12 mmol, 27.0 mg) were weighed into a reaction vial (10 mL) with a magnetic stir bar under air. HFIP (1.0 mL) was added, and the vial was sealed with a cap. The reaction mixture was stirred at 80° C. for 12 hours. Upon completion, the reaction mixture was cooled to room temperature and PPh$_3$ (0.12 mmol, 31.4 mg) was added. The reaction was stirred for another 1 h at 80° C. Upon completion, the reaction mixture was cooled to room temperature and diluted with EtOAc. Then the reaction mixture was filtered through a plug of celite. The solvent was removed under vacuum and the resulting mixture was purified by preparative thin-layer chromatography with EtOAc:MeOH=10:1 as the eluent.

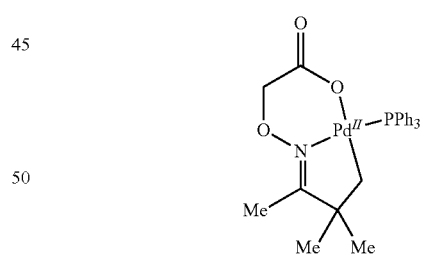

Palladacycle (3)

Substrate 1a was palladated following the general procedures. After purification by preparative thin-layer chromatography (EtOAc:MeOH=10:1 as eluent), 3 was obtained as a white solid (43.7 mg, 81%). $^1$H NMR (600 MHz, CDCl$_3$) δ 7.60-7.56 (m, 6H), 7.46-7.39 (m, 9H), 4.57 (s, 2H), 1.95 (s, 3H), 1.57 (d, J=3.6 Hz, 2H), 1.11 (s, 6H). $^{13}$C NMR (150 MHz, CDCl$_3$) δ 178.99, 172.54, 134.04 (d, J=12.0 Hz), 130.60, 128.57, 128.49, 76.00, 50.26, 40.35, 28.65, 12.24. HRMS (ESI-TOF) Calcd for $C_{26}H_{28}NO_3PPd$ [M+H]$^+$: 539.0842, found: 539.0850.

The Removal of Auxiliary

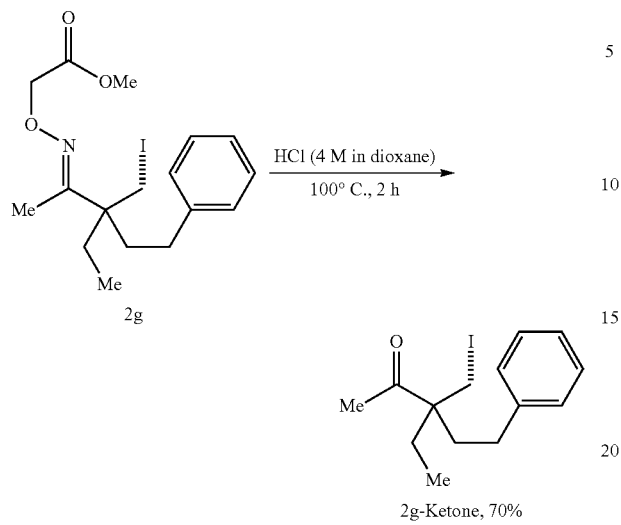

The removal of auxiliary: 2g (0.05 mmol, 20.9 mg) was weighed into a reaction vial (10 mL) with a magnetic stir bar under air. 0.5 mL of conc. HCl 4 M in dioxane was added, and the vial was sealed with a cap. The reaction mixture was stirred at 100° C. for 2 hours. Upon completion, the reaction mixture was cooled to room temperature and the solvent was removed under vacuum. The resulting mixture was purified by preparative thin-layer chromatography by using toluene/EtOAc (100:1) as the eluent to give 11.6 mg of 2g-Ketone (70% yield).

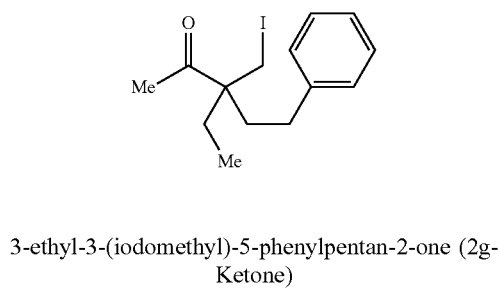

3-ethyl-3-(iodomethyl)-5-phenylpentan-2-one (2g-Ketone)

Colorless oil (11.6 mg, 70%). $^1$H NMR (600 MHz, CDCl$_3$) δ 7.30-7.28 (m, 2H), 7.22-7.17 (m, 3H), 3.50 (q, J=10.8 Hz, 2H), 2.51-2.46 (m, 1H), 2.30-2.26 (m, 1H), 2.23 (s, 3H), 2.04-1.98 (m, 1H), 1.96-1.90 (m, 1H), 1.82-1.73 (m, 2H), 0.80 (t, J=7.2 Hz, 3H). $^{13}$C NMR (150 MHz, CDCl$_3$) δ 209.25, 141.20, 128.55, 128.26, 126.19, 54.41, 38.04, 30.41, 28.63, 26.02, 12.15, 8.24. HRMS (ESI-TOF) Calcd for C$_{14}$H$_{20}$IO$^+$ [M+H]$^+$: 331.0553, found: 331.0560.

General Procedures for the C(sp$^3$)-H Arylation of Ketones: Substrate 1 (0.10 mmol, 18.7 mg), ArI (0.20 mmol, 52.4 mg for methyl p-iodobenzoate), Pd(OAc)$_2$ (0.01 mmol, 2.3 mg), and AgTFA (0.20 mmol, 44.2 mg) were weighed into a reaction vial (10 mL) with a magnetic stir bar under air. HFIP (1.0 mL) was added, and the vial was sealed with a cap. The reaction mixture was stirred at 120° C. for 20 hours. Upon completion, the reaction mixture was cooled to room temperature and diluted with EtOAc. Then the reaction mixture was filtered through a plug of silica gel and transferred to a reaction vial (10 mL) with a magnetic stir bar. The solvent was evaporated under vacuum. Anhydrous MeOH (1.0 mL) was added to the mixture. SOCl$_2$ (0.30 mmol, 22 μL) was added dropwise at room temperature. The vial was sealed with a cap. The reaction mixture was stirred at room temperature for 1 hour. Upon completion, the reaction mixture was cooled to room temperature and the solvent was removed under vacuum. The resulting mixture was purified by preparative thin-layer chromatography.

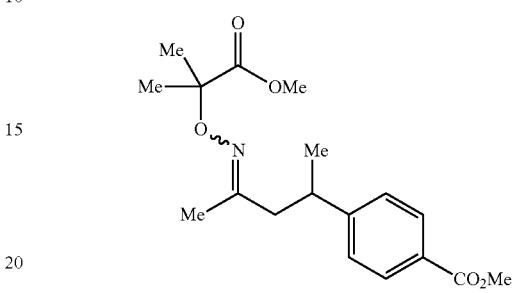

Methyl 4-(4-(((1-methoxy-2-methyl-1-oxopropan-2-yl)oxy)imino)pentan-2-yl)benzoate (2)

Substrate 1 was arylated following the general arylation procedure using methyl p-iodobenzoate as ArI. After purification by preparative thin-layer chromatography (Hexane:EtOAc=5:1 as eluent), 2 was obtained as E/Z (3.7:1) mixture (25.1 mg, 75%). $^1$H NMR (600 MHz, CDCl$_3$) of E isomer (major) δ 7.96-7.94 (m, 2H), 7.27-7.25 (m, 2H), 3.90 (s, 3H), 3.67 (s, 3H), 3.10 (sextet, J=7.2 Hz, 1H), 2.44 (ABqd, J$_1$=7.2 Hz, J$_2$=14.4 Hz, 2H), 1.79 (s, 3H), 1.42 (s, 3H), 1.39 (s, 3H), 1.24 (d, J=6.6 Hz, 3H). $^1$H NMR (600 MHz, CDCl$_3$) of Z isomer (minor) δ 7.98-7.96 (m, 2H), 7.32-7.30 (m, 2H), 3.90 (s, 3H), 3.72 (s, 3H), 3.27 (sextet, J=7.2 Hz, 1H), 2.60 (ABqd, J$_1$=7.2 Hz, J$_2$=13.2 Hz, 2H), 1.62 (s, 3H), 1.49 (s, 3H), 1.44 (s, 3H), 1.30 (d, J=7.2 Hz, 3H). $^{13}$C NMR (150 MHz, CDCl$_3$) of E/Z mixture δ 174.95, 174.92, 167.06, 156.49, 155.99, 151.95, 151.76, 129.74, 129.73, 128.07, 126.99, 126.96, 80.68, 51.95, 43.80, 37.91, 37.01, 36.79, 24.30, 24.17, 24.06, 24.03, 21.76, 21.52, 20.84, 14.50. HRMS (ESI-TOF) Calcd for C$_{18}$H$_{26}$NO$_5^-$ [M–H]$^-$: 336.1805, found: 336.1800.

DOCUMENTS CITED IN EXAMPLES (1) (a) Peter, M.; Gleiter, R.; Rominger, F.; Oeser, T. *Eur. J. Org. Chem.* 2004, 3212. (b) Maruyama, K.; Noguchi-Yachide, T.; Sugita, K.; Hashimoto, Y.; Ishikawa, M. *Bioorg. Med. Chem. Lett.* 2010, 20, 6661.
(2) Yang, Q.-L.; Li, Y.-Q.; Ma, C.; Fang, P.; Zhang, X.-J.; Mei, T.-S. *J. Am. Chem. Soc.* 2017, 139, 3293.
(3) Ushijima, S.; Dohi, S.; Moriyama, K.; Togo, H. *Tetrahedron*, 2012, 68, 1436.
(4) Ohkuma, T.; Sandoval, C. A.; Srinivasan, R.; Lin, Q.; Wei, Y.; Muniz, K.; Noyori, R. *J. Am. Chem. Soc.* 2005, 127, 8288.
(5) Li, X.; Li, L.; Tang, Y.; Zhong, L.; Cun, L.; Zhu, J.; Liao, J.; Deng, J. *J. Org. Chem.* 2010, 75, 2981.
(6) Yin, W.; He, H.; Zhang, Y.; Luo, D.; He, H. *Synthesis* 2014, 46, 2617.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of β-C(sp$^3$)-H iodination of a ketone having a p-hydrogen substituent, comprising:
   contacting the ketone and an aminooxyacetic acid in pyridine solvent to provide the corresponding oxime; then,
   contacting the oxime with iodine in the presence of a palladium(II) salt and phenyliodoniumacetate, in an aprotic solvent; then,
   hydrolyzing the oxime group under acidic conditions to provide the product β-C(sp$^3$)-iodoketone.

2. The method of claim 1 wherein the aminooxyacetic acid is aminooxyacetic acid or 2,2-dimethylaminooxyacetic acid.

3. The method of claim 1 wherein the palladium(II) salt is palladium(II) acetate or palladium(II)trifluoroacetate.

4. The method of claim 1 wherein the aprotic solvent is dioxane or 1,1,1,3,3,3-hexafluoroisopropanol.

5. The method of claim 1 wherein the oxime group is hydrolyzed in a solution of concentrated hydrochloric acid in dioxane.

6. A method of β-C(sp$^3$)-H arylation of a ketone having a β-hydrogen substituent, comprising:
   contacting the ketone and an aminooxyacetic acid in pyridine solvent to provide the corresponding oxime; then,
   contacting the oxime with an aryl iodide and silver trifluoroacetate in the presence of a palladium(II) salt, in an aprotic solvent; then,
   hydrolyzing the oxime group under acidic conditions to provide the product β-C(sp$^3$)-arylketone.

7. The method of claim 6 wherein the aminooxyacetic acid is aminooxyacetic acid or 2,2-dimethylaminooxyacetic acid.

8. The method of claim 6 wherein the palladium(II) salt is palladium(II) acetate or palladium(II)trifluoroacetate.

9. The method of claim 6 wherein the aprotic solvent is dioxane or 1,1,1,3,3,3-hexafluoroisopropanol.

10. The method of claim 6 wherein the oxime group is hydrolyzed in a solution of concentrated hydrochloric acid in dioxane.

* * * * *